US009353084B2

(12) United States Patent
Juhl et al.

(10) Patent No.: US 9,353,084 B2
(45) Date of Patent: May 31, 2016

(54) 2-AMINO 3,5,5-TRIFLUORO-3,4,5,6-TETRAHYDRO PYRIDINES AS BACE1 INHIBITORS FOR TREATMENT OF ALZHEIMER'S DISEASE

(71) Applicant: H. Lundbeck A/S, Valby-Copenhagen (DK)

(72) Inventors: Karsten Juhl, Greve (DK); Mauro Marigo, Skovlunde (DK); Lena Tagmose, Lyngby (DK); Thomas Jensen, Kobenhavn O. (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/625,658

(22) Filed: Feb. 19, 2015

(65) Prior Publication Data

US 2015/0232449 A1    Aug. 20, 2015

(30) Foreign Application Priority Data

Feb. 19, 2014  (DK) .................. 2014 00086
Jul. 1, 2014    (DK) .................. 2014 00349

(51) Int. Cl.
C07D 417/12    (2006.01)
C07D 211/72    (2006.01)
C07D 401/12    (2006.01)
C07D 413/12    (2006.01)

(52) U.S. Cl.
CPC ............ *C07D 401/12* (2013.01); *C07D 211/72* (2013.01); *C07D 413/12* (2013.01); *C07D 417/12* (2013.01)

(58) Field of Classification Search
CPC .. C07D 417/12; C07D 211/72; C07D 401/12; C07D 413/12

USPC ....................................... 514/255.05
See application file for complete search history.

(56) References Cited

U.S. PATENT DOCUMENTS 8,338,413 B1    12/2012  Rueeger

FOREIGN PATENT DOCUMENTS

| EP | 2703399 | 3/2014 |
|---|---|---|
| WO | WO03032970 A1 | 4/2003 |
| WO | WO03068747 A1 | 8/2003 |
| WO | 2011/154431 | 12/2011 |
| WO | 2012/095463 | 7/2012 |
| WO | 2012/095469 | 7/2012 |
| WO | 2012/139993 | 10/2012 |
| WO | 2012/168164 | 12/2012 |
| WO | 2013/027188 | 2/2013 |

(Continued)

OTHER PUBLICATIONS

Tobias Ginman et al., 2013, "Core Refinement toward Permeable B-Secretase (BACE-1) Inhibitors with Low hERG Activity", Journal of Medicinal Chemistry, vol. 56, pp. 4181-4205.

(Continued)

*Primary Examiner* — Janet L Andres
*Assistant Examiner* — Daniel Carcanague
(74) *Attorney, Agent, or Firm* — AuerbachSchrot LLC; Jeffrey I. Auerbach; William C. Schrot

(57) ABSTRACT

The present invention is directed to novel inhibitors of the BACE1 enzyme. Separate aspects of the invention are directed to pharmaceutical compositions comprising said compounds and uses of the compounds to treat disorders for which the reduction of Aβ deposits is beneficial such as Alzheimer's disease.

22 Claims, 1 Drawing Sheet

(56) References Cited

FOREIGN PATENT DOCUMENTS

| WO | 2013/142613 | 9/2013 |
|---|---|---|
| WO | 2014/056816 | 4/2014 |
| WO | 2014/065434 | 5/2014 |
| WO | 2014/134341 | 9/2014 |
| WO | 2015/124576 | 8/2015 |
| WO | 2015/156421 | 10/2015 |

OTHER PUBLICATIONS

Harald Hampel et al., 2009, "Beta-site amyloid precursor protein cleaving enzyme 1 (BACE1) as a biological candidate marker of Alzheimer's disease", The Scandinavian Journal of Clinical & Laboratory Investigation, vol. 69, No. 1, pp. 8-12.

Fredrik Jeppsson, et al., 2012, "Discovery of AZD3839, a Potent and Selective BACE1 Inhibitor Clinical Candidate for the Treatment of Alzheimer Disease", The Journal of Biological Chemistry, vol. 287, No. 49, p. 41245-41257.

Masuo Ohno et al, 2004, "BACE1 Deficiency Rescues Memory Deficits and Cholinergic Dysfunction in a Mouse Model of Alzheimer's Disease", Neuron, vol. 41, pp. 27-33.

Masuo Ohno, et al., 2007, "BACE 1 gene deletion prevents neuron loss and memory deficits in 5XFAD APP/PS1 transgenic mice", Neurobiology of Disease., (26), pp. 134-145.

Michael Willem et al., 2009, "Function, regulation and therapeutic properties of B-secretase (BASE1)", Seminars in Cell & Developmental Biology, (20), pp. 175-182.

Thomas J. Woltering et al., 2013, "BACE1 inhibitors: A head group scan on a series of amides", Bioorganic & Medicinal Chemistry Letters, (23) pp. 4239-4243.

Yoshio Hamada et al., 2009, "Recent progress in the drug discovery of non-peptidic BACE1 inhibitors", Expert Opinion on Drug Discovery, vol. 4. No. 4, pp. 391-416.

Hans Hilpert et al., 2013, "B-Secretase (BACE1) Inhibitors with High In Vivo Efficacy Suitable for Clinical Evaluation in Alzheimer's Disease", Journal of Medicinal Chemistry, vol. 56, pp. S2-S44.

Hans Hilpert et al., 2013, "B-Secretase (BACE1) Inhibitors with High In Vivo Efficacy Suitable for Clinical Evaluation in Alzheimer's Disease", Journal of Medicinal Chemistry, vol. 56, No. 10, pp. 3980-3995.

Michael S. Malamas et al., 2010, "Novel pyrrolyl 2-aminopyridines as potent and selective human B-secretase (BACE 1) inhibitors", Bioorganic & Medicinal Chemistry letters, vol. 20, pp. 2068-2073.

Gary Probst et al., 2012, "Small-molecule BACE1 inhibitors: a patent literature review (2006-2011)", Expert Opinion on Therapeutic Patents, vol. 22, No. 5, pp. 511-540.

So-Young Jeon et al., 2003, "Green Tea Catechins as a BACE1 (B-Secretase) Inhibitor", Bioorganic & Medicinal Chemistry Letters, vol. 13, pp. 3905-3908.

International Search Report issued Apr. 30, 2015 in International Application No. PCT/EP2015/053327 filed Feb. 17, 2015.

Asuni, A. et al. (2007) "Immunotherapy Targeting Pathological Tau Conformers in a Tangle Mouse Model Reduces Brain Pathology with Associated Functional Improvements," J. Neurosci. 27:9115-9129.

Berge, S.M. et al. (1977) "Pharmaceutical Salts," J. Pharm. Sci. 66:1-19.

Boutajangout, A. et al. (2010) "Immunotherapy Targeting Pathological Tau Prevents Cognitive Decline in a New Tangle Mouse Model," J. Neurosci. 30949):16559-16566.

Boutajangout, A. et al. (2011) "Targeting Hyperphosphorylated Tau Protein with a Monoclonal Antibody at an Advanced Stage of Tau Pathology Improves Cognition in a Mouse Model," 7(4,suppl):S480-S481.

International Search Report PCT/EP2015/076017 (2016) (5 pages).

Jacobsen, H. et al. (2014) "Combined Treatment with a BACE Inhibitor and Anti-Aβ Antibody Gantenerumab Enhances Amyloid Reduction in APPLondon Mice," J. Neurosci. 34(35):11621-11630.

Kumar, A. et al. (2015) "A Review on Alzheimer's Disease Pathophysiology and Its Management: An Update," Pharmacol. Reporting 67:195-203.

Melis, V . et al. (2015) "Effects of Oxidized and Reduced Forms of Methylthioninium in Two Transgenic Mouse Tauopathy Models," Behav. Pharmacol. 26:353-368.

Oehlrich, D. et al. (2014) "The Evolution of Amidine-Based Brain Penetrant BACE1 Inhibitors," Bioorganic & Medicinal Chem. Lett. 24(9):2033-2045.

Sheline, Y.I. et al. (2014) "An Antidepressant Decreases CSF Aβ Production in Healthy Individuals and in Transgenic AD Mice," Sci. Transl. Med. 6(236):236re4; pp. 1-10.

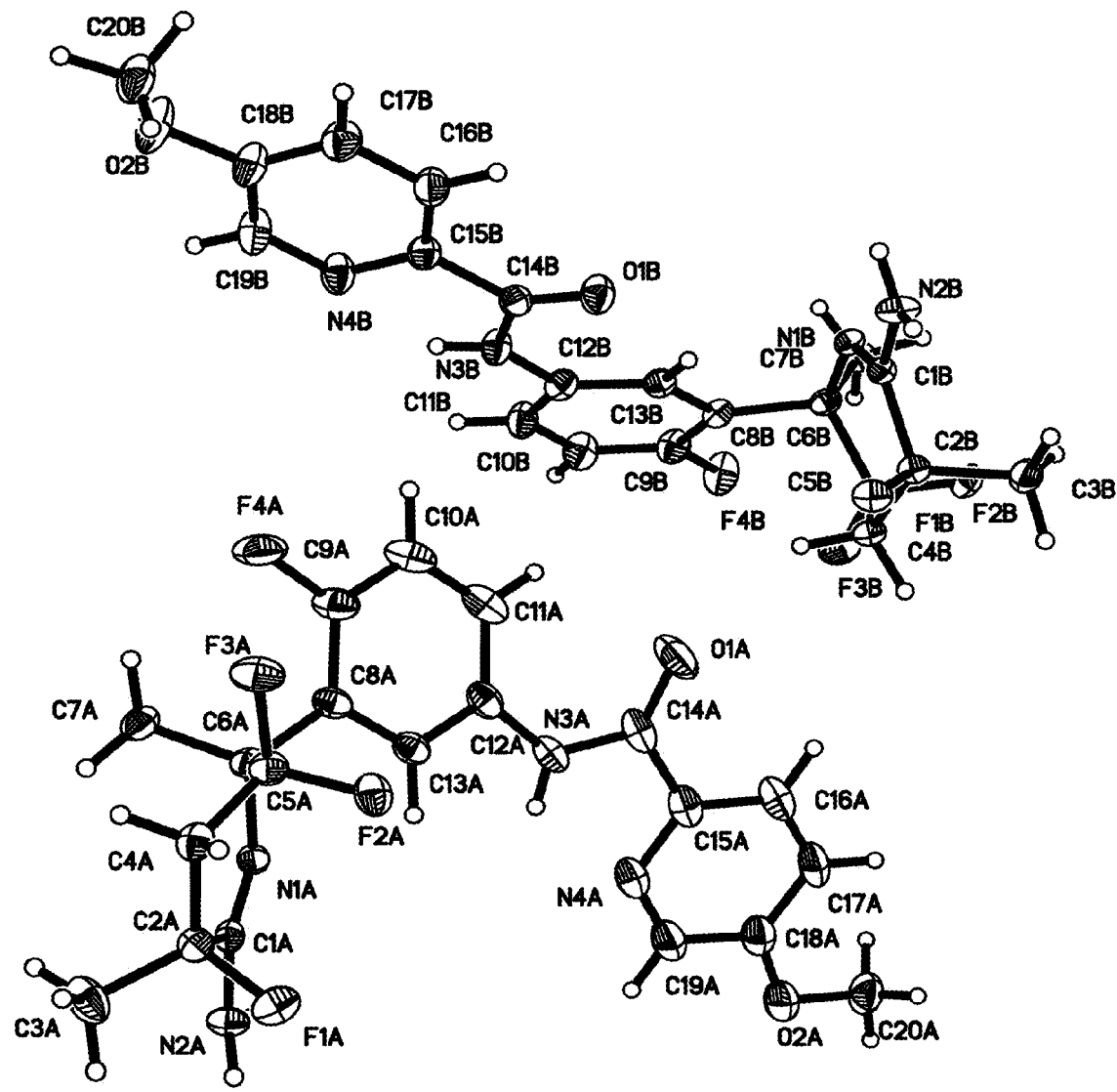

2-AMINO 3,5,5-TRIFLUORO-3,4,5,6-TETRAHYDRO PYRIDINES AS BACE1 INHIBITORS FOR TREATMENT OF ALZHEIMER'S DISEASE

CROSS-REFERENCE TO RELATED APPLICATIONS

The present application claims priority of Danish Patent Application No. PA201400349, filed Jul. 1, 2014 and Danish Patent Application No. PA201400086, filed Feb. 19, 2014. Each of these applications is hereby incorporated by reference in its entirety.

FIELD OF THE INVENTION

The present invention provides compounds which act as BACE1 inhibitors. Separate aspects of the invention are directed to pharmaceutical compositions comprising said compounds and uses of the compounds to treat Alzheimer's disease.

BACKGROUND ART

Dementia is a clinical syndrome characterized by deficits in multiple areas of cognition that cannot be explained by normal aging, a noticeable decline in function, and an absence of delirium. In addition, neuropsychiatric symptoms and focal neurological findings are usually present. Dementia is further classified based on etiology Alzheimer's disease (AD) is the most common cause of dementia, followed by mixed AD and vascular dementia, vascular dementia, Lewy body dementia (DLB), and fronto-temporal dementia.

β-Amyloid deposits and neurofibrillary tangles are considered to be major pathologic characterizations associated with AD which is characterized by the loss of memory, cognition, reasoning, judgment, and orientation. Also affected, as the disease progresses, are motor, sensory and linguistic abilities until global impairment of multiple cognitive functions occurs. β-Amyloid deposits are predominantly an aggregate of Aβ peptide, which in turn is a product of the proteolysis of amyloid precursor protein (APP) as part of the β-amyloidogenic pathway, Aβ peptide results from the cleavage of APP at the C-terminals by one or more γ-secretases and at the N-terminus by β-secretase enzyme (BACE1) also known as aspartyl protease 2. BACE1 activity is correlated directly to the generation of Aβ peptide from APP.

Studies indicate that the inhibition of BACE1 impedes the production of Aβ peptide. Further, BACE1 co-localizes with its substrate APP in Golgi and endocytic compartments (Willem M, et al. Semin. Cell Dev. Biol, 2009, 20, 175-182). Knock-out studies in mice have demonstrated the absence of amyloid peptide formation while the animals are healthy and fertile (Ohno M, et al. Neurobiol. Dis., 2007, 26, 134-145). Genetic ablation of BACE1 in APP-overexpressing mice has demonstrated absence of plaque formation, and the reversal of cognitive deficits (Ohno M, et al. Neuron; 2004, 41, 27-33). BACE1 levels are elevated in the brains of sporadic AD patients (Hampel and Shen, Scand. J. Clin. Lab. Invest. 2009, 69, 8-12).

These convergent findings indicate that the inhibition of BACE1 may be a therapeutic target for the treatment of AD as well as disorders for which the reduction of Aβ deposits is beneficial.

At the 2012 Alzheimer's Association International Conference in Vancouver, several drug developers announced their BACE1 inhibitors in clinical trials. Eli Lilly scientists reported preclinical research on LY2886721 which had entered a Phase II study. Merck presented a series of posters detailing the Phase I studies of its BACE inhibitor, MK-8931, and announced the start of separate Phase III studies which will test the compound for two years in people with prodromal Alzheimer's disease. Numerous patent applications directed to BACE1 inhibitors have been published over the past several years.

AstraZeneca announced the discovery of AZD3839, a potent and selected BACE1 inhibitor clinical candidate for the treatment of AD (Jeppsson, F., et al. JBC, 2012, 287, 41245-41257) in October 2012. The effort which led to the discovery of AZD3839 was further described in Ginman, T., et al. Journal of Medicinal Chemistry, 2013, 56, 4181-4205. The Ginman publication describes the issues which were overcome in connection with the discovery and identification of AZD3839. These issues related to poor blood brain barrier penetration and P-glycoprotein mediated efflux of the compounds resulting in lack of brain exposure.

The Ginman manuscript hypothesized that the differences would largely be due to the core structures and Structure Activity Relationship data was provided wherein the in vitro properties on the reported compounds were given into four tables according to core sub-types. In table 4, a series of amidine containing compounds are described that were considered interesting from an activity perspective. However, the data suggests that the amidine containing core did not exhibit a favourable blood brain barrier permeability profile.

Researchers from Hoffmann-La Roche and Siena Biotech also reported the discovery of amidine containing compounds (Woltering, T. J., et al. Bioorg. Med. Chem. Left. 2013, 23, 4239-4243). These compounds (compounds 17 and 18 in the paper) were found not to have any in vivo effect (lack of Aβ40 reduction in brain in wild type mice).

SUMMARY OF THE INVENTION

Contrary to the teachings of Ginman, et al. and Woltering, T. J., et al., the inventors have discovered a series of amidine compounds which are brain penetrant and are thus able to inhibit BACE1 in the brain after peripheral dose of said compounds. Accordingly, the present invention relates to novel compounds having BACE1 inhibitory activity, to their preparation, to their medical use and to medicaments comprising them.

An objective of the present invention is to provide compounds that inhibit BACE1. Accordingly, the present invention relates to compounds of Formula I.

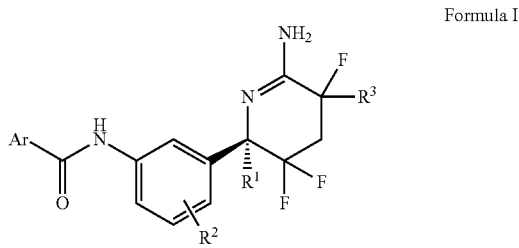

Formula I

Ar is selected from the group consisting of phenyl, pyridyl, pyrimidyl, pyrazinyl, imidazolyl, pyrazolyl, 1,2,4-triazolyl, thiophenyl, thiazolyl, oxazolyl, isoxazolyl, 1,3,4-thiadiazolyl, isothiazolyl, 1,3,4-oxadiazolyl, 1,2,4-oxadiazolyl, furazanyl and 1,2,4-thiadiazolyl and where the Ar is optionally substituted with one or more halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy;

$R^1$ is $C_1$-$C_3$ alkyl or $C_1$-$C_3$ fluoroalkyl;

$R^2$ is hydrogen, halogen, $C_1$-$C_3$ fluoroalkyl or $C_1$-$C_3$ alkyl; and $R^3$ is $C_1$-$C_3$ alkyl; or a pharmaceutically acceptable salt thereof.

The present invention further provides a pharmaceutical composition comprising a therapeutically effective amount of a compound of Formula I and a pharmaceutically acceptable carrier.

The present invention provides a method of treating a subject suffering from Alzheimer's disease comprising administering to the subject a therapeutically effective amount of a compound of Formula I.

The present invention is directed to the use of a compound as defined in Formula I for the manufacture of a medicament for treating Alzheimer's disease.

Further embodiments of the invention are provided immediately below:

In one embodiment, the compound is of formula Ia

Formula Ia or a pharmaceutically acceptable salt thereof.

In one embodiment, $R^1$ is $CH_3$.

In one embodiment, $R^2$ is F or H.

In one embodiment, $R^3$ is $CH_3$.

In one embodiment, Ar is optionally substituted with one or more F, Cl, CN, $C_1$-$C_3$ alkyl, $C_1$-$C_3$ fluoroalkyl or $C_1$-$C_3$ alkoxy.

In one embodiment, the stereochemistry is (2R,5S).

In one embodiment, Ar is optionally substituted phenyl.

In one embodiment, Ar is optionally substituted pyridyl.

In one embodiment, Ar is optionally substituted pyrimidyl.

In one embodiment, Ar is optionally substituted pyrazinyl.

In one embodiment, Ar is optionally substituted imidazolyl.

In one embodiment, Ar is optionally substituted pyrazolyl.

In one embodiment, Ar is optionally substituted 1,2,4-triazolyl.

In one embodiment, Ar is optionally substituted thiophenyl.

In one embodiment, Ar is optionally substituted oxazolyl.

In one embodiment, Ar is optionally substituted isoxazolyl.

In one embodiment, Ar is optionally substituted 1,3,4-thiadiazolyl.

In one embodiment, Ar is optionally substituted thiazolyl.

In one embodiment, Ar is optionally substituted isothiazolyl.

In one embodiment, Ar is optionally substituted 1,3,4-oxadiazolyl.

In one embodiment, Ar is optionally substituted 1,2,4-oxadiazolyl.

In one embodiment, Ar is optionally substituted furazanyl.

In one embodiment, Ar is optionally substituted 1,2,4-thiadiazolyl.

In separate embodiments of the invention, the compound is selected from one of the exemplified compounds disclosed in the Experimental Section.

A separate embodiment is directed to a pharmaceutical composition comprising the compound or a pharmaceutically acceptable salt thereof and a pharmaceutically acceptable carrier.

Another embodiment is directed to a method of treating Alzheimer's disease comprising administering a therapeutically effective amount of the compound.

Yet another embodiment is directed to a use of a compound for the manufacture of a medicament for treating Alzheimer's disease.

One embodiment is a compound for use in therapy.

Yet another embodiment is directed to a compound for use in the treatment of Alzheimer's disease. Included also in this invention are isotopically labelled compounds, which are identical to those claimed in formula I, where one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, fluorine, chlorine and iodine, such as $^2H$, $^3H$, $^{13}C$, $^{11}C$, $^{14}C$, $^{15}N$, $^{18}O$, $^{17}O$, $^{35}S$, $^{18}F$, $^{36}Cl$ and $^{125}I$, respectively. Compounds of the invention, prodrugs thereof, and pharmaceutically acceptable salts of said compounds or said prodrugs which contain the aforementioned isotopes and/or other isotopes of other atoms are within the scope of this invention. Certain isotopically labelled compounds of the invention, such as those with radioactive isotopes incorporated including but not limited to $^3H$ and $^{14}C$, are useful in drug and/or substrate tissue distribution assays.

BRIEF DESCRIPTION OF THE DRAWINGS

FIG. 1 shows the two molecules in the asymmetric unit as found in the crystal structure. The X-ray method used cannot distinguish between hydrogen ($^1H$) and deuterium (D or $^2H$). Hence, the deuterium atoms in the d3-methoxy group are depicted as hydrogen.

DETAILED DESCRIPTION OF THE INVENTION

The present invention is based on the discovery that the compounds of Formula I are inhibitors of BACE1, and as such, are useful for the treatment of related disorders. Certain aspects of the invention are explained in greater detail below but this description is not intended to be a detailed catalog of all the different ways in which the invention may be implemented, or all the features that may be added to the present invention. Hence, the following specification is intended to illustrate some embodiments of the invention, and not to exhaustively specify all permutations, combinations and variations thereof.

As used herein, the term "$C_1$-$C_6$ alkyl" refers to a straight chained or branched saturated hydrocarbon having from one to six carbon atoms, inclusive. Examples of such substituents include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "straight chained or branched $C_1$-$C_3$ alkyl" refers to a saturated hydrocarbon having from one to three carbon atoms, inclusive. Examples of such substituents include, but are not limited to, methyl, ethyl and n-propyl.

Likewise, the term "$C_1$-$C_6$ alkoxy" refers to a straight chained or branched saturated alkoxy group having from one to six carbon atoms, inclusive, with the open valency on the oxygen. Examples of such substituents include, but are not limited to, methoxy, ethoxy, n-butoxy, t-butoxy and n-hexyloxy. The "$C_1$-$C_6$ alkoxy" is optionally substituted with one or more fluorine atoms.

As used herein, the term "$C_1$-$C_6$ fluoroalkyl" refers to a straight chained or branched saturated hydrocarbon having from one to six carbon atoms inclusive substituted with one or more fluorine atoms. Examples of such substituents include, but are not limited to, trifluoromethyl, pentafluoroethyl, 1-fluoroethyl, monofluoromethyl, difluoromethyl, 1,2-difluoroethyl and 3,4 difluorohexyl. Similarly, the term "straight chained or branched $C_1$-$C_3$ fluoroalkyl" refers to a saturated hydrocarbon having from one to three carbon atoms, inclusive, substituted with one or more fluorine atoms per carbon atom.

The term "halogen" refers to fluorine, chlorine, bromine and iodine.

The term "$C_{2-6}$-alkenyl" refers to a branched or unbranched alkenyl group having from two to six carbon atoms and one double bond, including but not limited to ethenyl, propenyl, and butenyl.

The term "$C_{2-6}$-alkynyl" shall mean a branched or unbranched alkynyl group having from two to six carbon atoms and one triple bond, including but not limited to ethynyl, propynyl and butynyl.

Throughout the description and the claims, each compound number corresponds to the number of the experiment in which the method of manufacture is disclosed. Compounds 4 and 18 have resynthesized using a modified method of manufacture as disclosed in examples 4a and 18a.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "effective amount" is the amount of the combination sufficient to cause the intended biological effect.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a neurodegenerative or cognitive disease or disorder.

In an embodiment of the invention, the neurodegenerative or cognitive disease or disorder is Alzheimer's disease, mild cognitive impairment, Trisomy 21 (Down Syndrome), cerebral amyloid angiopathy, Hereditary Cerebral Hemorrhage with Amyloidosis of the Dutch-Type (HCHWA-DT), degenerative dementia, amyotrophic lateral sclerosis, traumatic brain injury or stroke.

In an embodiment, the disease or disorder is a peripheral amyloidosis, such as amyloid neuropathy or pancreatitis.

In an embodiment, the disease or disorder is peripheral nerve damage.

The present invention provides a method of treating Alzheimer's disease in a patient comprising administering to a patient in need of such treatment a therapeutically effective amount of at least one compound of formula I.

The present invention further provides a method of inhibiting BACE1 in a patient comprising administering to a patient in need thereof a therapeutically effective amount of at least one compound of formula I.

The present invention also provides a method of inhibiting β-secretase mediated cleavage of amyloid precursor protein comprising administering to a patient in need of such treatment a therapeutically effective amount of at least one compound of formula I.

In further embodiments, the present invention provides the use of a compound of formula I for the manufacture of a medicament for the treatment of Alzheimer's disease. The present invention also provides the use of a compound of formula I for the manufacture of a medicament for the inhibition of BACE1. The present invention further provides the use of a compound of formula I for the manufacture of a medicament for the inhibition of production or accumulation of Aβ peptide.

The invention also provides a compound of formula I for use in therapy of a patient, for example, in the treatment of Alzheimer's disease or to slow the progression of a patient's mild cognitive impairment to Alzheimer's disease.

In a further embodiment, the invention provides a pharmaceutical formulation adapted for any of the above treatments and uses.

In some embodiments, the mammal of the method of the invention is a human.

In other embodiments, the patient of the method of the invention is a human patient.

In some embodiments of the invention, at least one symptom of the neurodegenerative or cognitive disease or disorder is treated.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., J. Pharm. Sci., 1977, 66, 2.

Furthermore, the compounds of this invention may exist in unsolvated as well as in solvated forms with pharmaceutically acceptable solvents such as water, ethanol and the like.

The compounds of the present invention may have one or more asymmetric centres and it is intended that any optical isomers (i.e. enantiomers or diastereomers), as separated, pure or partially purified optical isomers, and any mixtures thereof including racemic mixtures, i.e. a mixture of stereoisomeres, are included within the scope of the invention.

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Pharmaceutical Compositions

The present invention further provides a pharmaceutical composition comprising a therapeutically effective amount of a compound of Formula I and a pharmaceutically acceptable carrier. The present invention also provides a pharmaceutical composition comprising a therapeutically effective amount of one of the specific compounds disclosed in the description, such as in the experimental section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{th}$ Edition, Troy, Ed., Lippincott Williams & Wilkins, Baltimore, Md., USA.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs. Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.01 to about 100 mg/kg body weight per day.

The compounds of this invention are generally utilized as the free substance or as a pharmaceutically acceptable salt thereof. One example is an acid addition salt of a compound having the utility of a free base. When a compound of Formula I contains a free base such salts are prepared in a conventional manner by treating a solution or suspension of a free base of Formula I with a molar equivalent of a pharmaceutically acceptable acid. Representative examples of suitable organic and inorganic acids are described above.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of Formula I and a pharmaceutically acceptable carrier are then readily administered in a variety of dosage forms suitable for the disclosed routes of administration. The formulations may conveniently be presented in unit dosage form by methods known in the art of pharmacy.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

Experimental Section

The compounds of the present invention of the general formula I, wherein $R^1$, $R^2$, $R^3$ and Ar are as defined above, can be prepared by the methods outlined in the following reaction schemes 1-3 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

For example, Schemes 1-2 describe the use of selective protecting groups during the synthesis of the compounds of the invention. One skilled in the art would be able to select the appropriate protecting group for a particular reaction. Moreover, it may be necessary to incorporate protection and deprotection strategies for substituents such as amino, amido, carbaldehyde and hydroxyl groups in the synthetic methods described below to synthesize the compounds of Formula I. Methods for protection and deprotection of such groups are well known in the art, and may be found in T. Green, et al., Protective Groups in Organic Synthesis, 1991, 2$^{nd}$ Edition, John Wiley & Sons, New York.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers.

Analytical LC-MS data were obtained using the following methods.

Method A:

LC-MS were run on Waters Acquity UPLC-MS consisting of Waters Acquity including column manager, binary solvent manager, sample organizer, PDA detector (operating at 254 nm), ELS detector, and TQ-MS equipped with APPI-source operating in positive ion mode.

LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile+5% water+0.05% trifluoroacetic acid. Gradient: 0.00 min: 10% B; 1.00 min: 100% B; 1.01 min: 10% B; 1.15 min: 10% B. Total run time: 1.15 min.

Method B:

LC-MS were run on Waters Aquity UPLC-MS consisting of Waters Aquity including column manager, binary solvent manager, sample organizer, PDA detector (operating at 254 nM), ELS detector, and SQ-MS equipped with APPI-source operating in positive ion mode.

LC-conditions: The column was Acquity UPLC BEH C18 1.7 μm; 2.1×150 mm operating at 60° C. with 0.6 ml/min of a binary gradient consisting of water+0.05% trifluoroacetic acid (A) and acetonitrile+5% water+0.03% trifluoroacetic acid. Gradient: 0.00 min: 10% B; 3.00 min: 99.9% B; 3.01 min: 10% B; 3.60 min: 10% B. Total run time: 3.60 min.

$^1$H NMR spectra were recorded at 600 MHz on a Bruker Avance AV-III-600 instrument. Chemical shift values are expressed in ppm-values relative. The following abbreviations are used for multiplicity of NMR signals: s=singlet, d=doublet, t=triplet, q=quartet, dd=double doublet, ddd=double double doublet, dt=double triplet, br=broad, and m=multiplet.

As an example and wherein R$^2$ is fluorine in the ortho position of the phenyl ring, compounds of the general formulae XVIa and XVIb may be prepared as shown in Scheme 1.

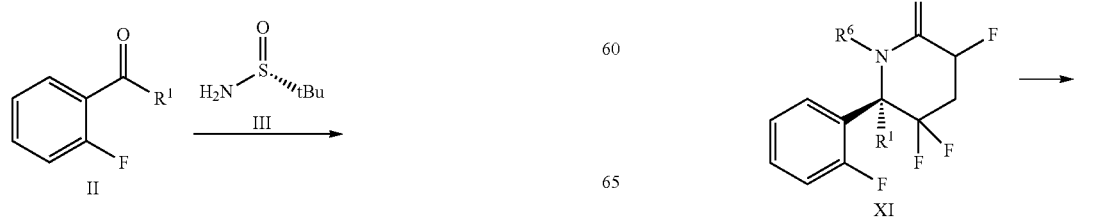

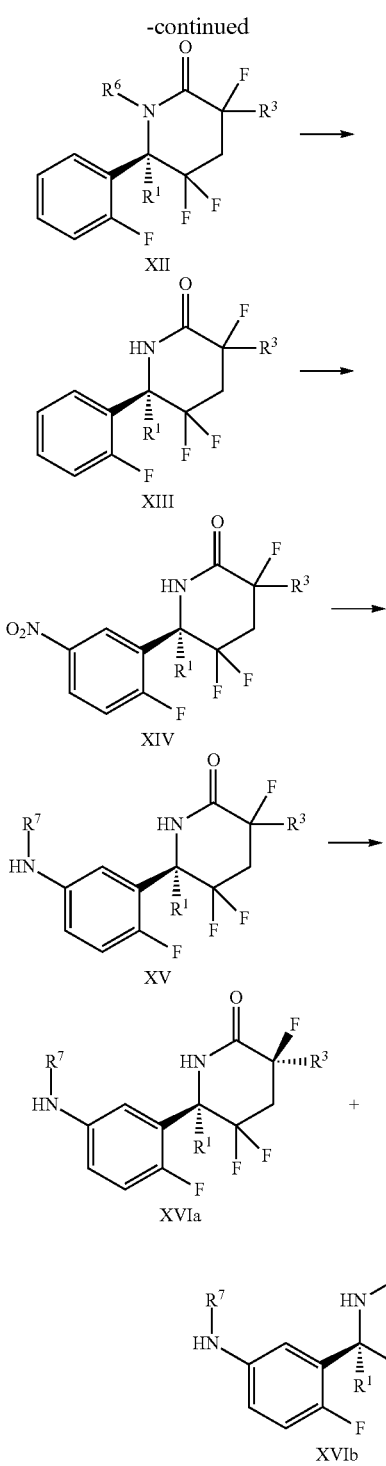

and tris(triphenylphosphine)rhodium(I) chloride gives compounds of the general formula VI. Compounds of the general formula VII are obtained from compounds of the general formula VI by treatment with a reducing agent such as diisobutylaluminium hydride. In some cases compound VII might be in the hydrate form or an oligomeric form thereof. Treatment of compounds of the general formula VII with conditions such as ethyl 2-(diethoxyphosphoryl)-2-fluoroacetate in the presence of lithium chloride and a base such as N,N-diisopropylethylamine gives compounds of the general formula VIII. Compounds of the general formula IX are obtained by hydrogenation of compounds of the general formula VIII in the presence of a catalyst such as palladium on carbon. Compounds of the general formula X are obtained by treatment of compounds of the general formula IX with an acid such as hydrochloric acid in methanol followed by treatment with potassium carbonate in methanol. Compounds of the general formula XI are obtained by treatment of compounds of the general formula X with di-tert-butyl dicarbonate in the presence of a catalytic amount of DMAP (N,N-dimethyl-4-amino-pyridine). Compounds of the general formula XII are obtained by treatment of compounds of the general formula XI with a base such as lithium hexamethyldisilazide follow by alkylation with a alkylhalide. Deprotection of compounds of the general formula XII gives compounds of the general formula XIII which can be nitrated using nitric acid to give compounds of the general formula XIV. Reduction of the nitro group of compounds of the general formula XIV followed by protection of the formed aniline moiety gives compounds of the general formula XX. Treatment of compounds of the general formula XV with a reagent such as Lawesson's reagent (2,4-bis(4-methoxyphenyl)-1,3,2,4-dithiadiphosphetane-2,4-disulfide) followed by chromatographic separation gives compounds of the general formulae XVIa and XVIb.

Compounds of the general formula I may be prepared as shown in Scheme 2.

Scheme 2

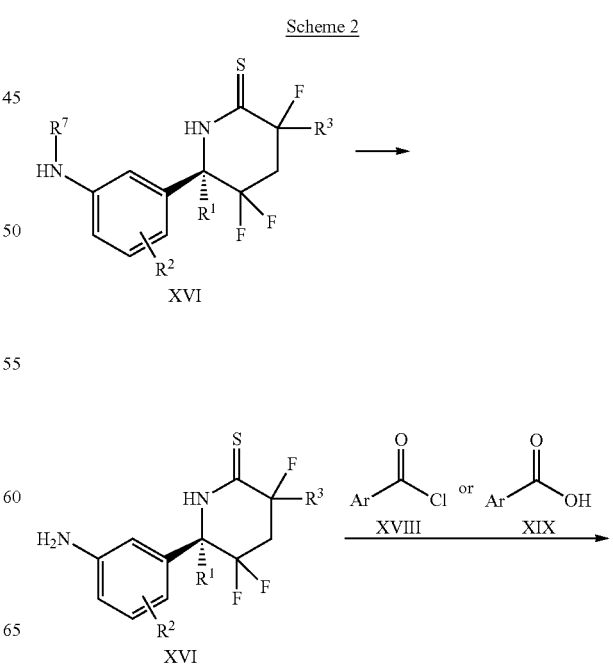

where $R^1$ and $R^3$ are as defined under formula I, $R^4$ and $R^5$ are an alkyl group such as methyl or ethyl and $R^6$ and $R^7$ are independently selected amine protection groups such as a tert-butoxy carbonyl group.

Compounds of the general formula IV (Scheme 1) may be prepared by reacting compounds of the general formula II with a sulfinamide such as III in the presence of a Lewis acid/drying agent such as titanium tetraethoxide. Treatment of compounds of the general formula IV with compounds of the general formula V such as ethyl bromodifluoroacetate in the presence of Zn powder or in the presence of diethyl zinc -continued

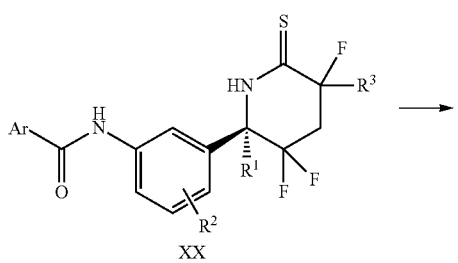

XX

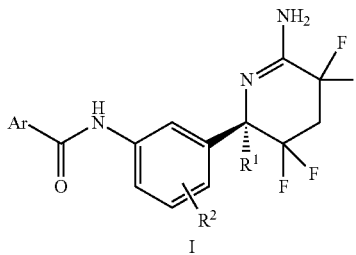

I where $R^1$, $R^2$, $R^3$ and Ar are as defined under formula I and $R^7$ is an amine protection groups such as a tert-butoxy carbonyl group.

Compounds of the general formula XVII (Scheme 2) can be obtained by deprotection of compounds of the general formula XVI. Compounds of the general formula XX may be prepared by reacting compounds of the general formula XVII with a carboxylic acid chloride of general formula XVIII or by reaction with a carboxylic acid of general formula XIX using procedures known to chemists skilled in the art. Treatment of compounds of the general formula XX with ammonia gives compounds of the general formula I. In some cases, the addition of an oxidizing reagent such as tert-butyl hydroperoxide might be necessary to facilitate the reaction.

Compounds of the general formula I may be prepared as shown in Scheme 3.

Scheme 3

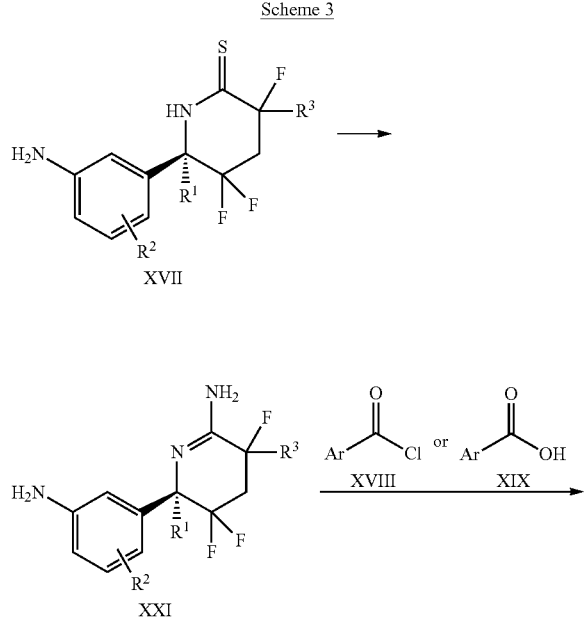

-continued

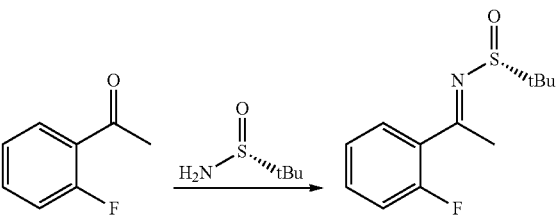

I where $R^1$, $R^2$, $R^3$ and Ar are as defined under formula I.

Compounds of the general formula XXI (Scheme 3) can be obtained by treatment of compounds of the general formula XVII with ammonia. Compounds of the general formula I may be prepared by reacting compounds of the general formula XXI with a carboxylic acid chloride of general formula XVIII or by reaction with a carboxylic acid of general formula XIX using procedures known to chemists skilled in the art.

Preparation of Intermediates

INTERMEDIATE: (R)—N-(1-(2-fluorophenyl)ethylidene)-2-methylpropane-2-sulfinamide 1-(2-Fluorophenyl)ethanone (15 g, 109 mmol) and (R)-2-methylpropane-2-sulfinamide (15.79 g, 130 mmol) were placed in a round bottom flask fitted with a reflux condenser. Tetrahydrofuran (90 ml) (dried over 4 Å MS) was added followed by Ti(OEt)$_4$ (49.5 g, 217 mmol) and the resulting yellow solution was stirred at gentle reflux overnight. The reaction was allowed to cool to room temperature and concentrated under reduced pressure. The residue was dissolved in ethyl acetate (200 mL) and brine (100 mL) was added dropwise while stirring vigorously. The addition of brine resulted in immediate formation of copious amounts of a white precipitate. After 10 min stirring at room temperature the suspension was filtered through a plug of celite using ethyl acetate for elution. The filtrate was transferred to a separation funnel, the layers were separated, and the organic layer was washed with brine (150 mL). The organic layer was dried over MgSO$_4$, filtered and concentrated under reduced pressure and was purified using a CombiFlash system (330 g SiO$_2$, gradient elution; heptanes:ethyl acetate 100:0→70:30) to afford (R)—N-(1-(2-fluorophenyl)ethylidene)-2-methylpropane-2-sulfinamide (20.6 g, 70.8% yield) $^1$H NMR (600 MHz, CDCl$_3$) δ 7.69 (t, J=7.1 Hz, 1H), 7.43 (dd, J=13.0, 6.0 Hz, 1H), 7.18 (td, J=7.7, 1.0 Hz, 1H), 7.11 (ddd, J=11.3, 8.3, 0.8 Hz, 1H), 2.78 (d, J=3.4 Hz, 3H), 1.32 (s, 9H).

INTERMEDIATE: (R)-ethyl 3-((R)-1,1-dimethylethylsulfinamido)-2,2-difluoro-3-(2-fluorophenyl)-butanoate

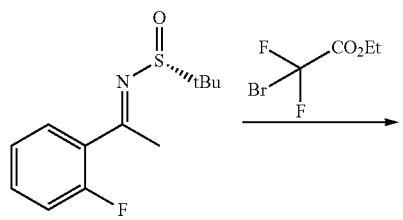

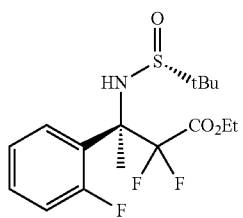

Tris(triphenylphosphine)rhodium(I) chloride (1.50 g, 1.62 mmol) was placed in a dry round bottom flask. The flask was evacuated and filled with argon (×3). (R)—N-(1-(2-Fluorophenyl)ethylidene)-2-methylpropane-2-sulfinamide (15.6 g, 64.6 mmol) was dissolved in tetrahydrofuran (265 ml) (dried over 4 Å MS) and added to the reaction flask followed by ethyl bromodifluoroacetate (26.2 g, 16.6 ml, 129 mmol). The dark red/orange reaction mixture was cooled to 0° C. using an ice/water bath. Diethyl zinc (126 ml, 126 mmol, 1 M in hexane) was added in a dropwise manner. Upon complete addition the reaction was stirred at 0° C. for an additional 1 h, the cooling was removed and the reaction was stirred at room temperature overnight. The reaction was diluted with ethyl acetate (250 mL) and quenched with saturated aqueous NaHCO₃ (100 mL). The resulting suspension was filtered through a plug of celite, the phases were separated, and the organic layer was dried over MgSO₄, filtered, and concentrated under reduced pressure. The crude material was purified using a CombiFlash system (330 g SiO₂, gradient elution; heptanes:ethyl acetate 100:0→60:40) to afford (R)-ethyl 3-((R)-1,1-dimethylethylsulfinamido)-2,2-difluoro-3-(2-fluorophenyl)butanoate (14.1 g, 59.7% yield). The stereochemistry was assigned based on literature precedence (WO2012110459) ¹H NMR (600 MHz, CDCl₃) δ 7.46 (t, J=8.0 Hz, 1H), 7.41-7.35 (m, 1H), 7.19-7.14 (m, 1H), 7.07 (dd, J=13.0, 8.2 Hz, 1H), 4.65 (d, J=2.6 Hz, 1H), 4.25 (q, J=7.2 Hz, 2H), 2.07 (s, 3H), 1.30-1.21 (m, 12H).

INTERMEDIATE: (R)-ethyl 5-((R)-1,1-dimethylethylsulfinamido)-2,4,4-trifluoro-5-(2-fluorophenyl)-hex-2-enoate

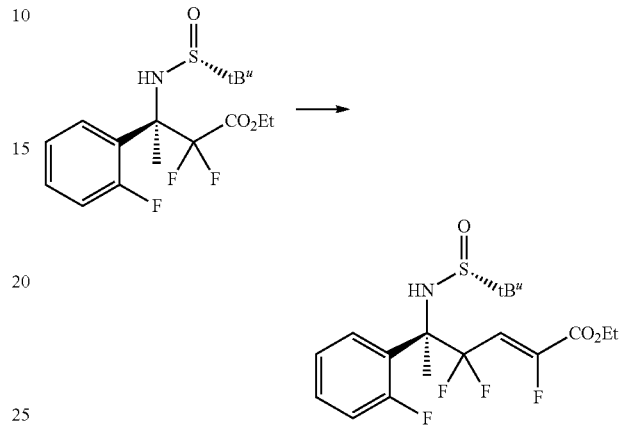

(R)-Ethyl 3-((R)-1,1-dimethylethylsulfinamido)-2,2-difluoro-3-(2-fluorophenyl)butanoate (7.6 g, 20.8 mmol) was dissolved in toluene (100 ml) (dried over 4 Å MS) and transferred to a dry round bottom flask. The solution was cooled to −78° C. using a dry ice/acetone bath. DIBAL-H (41.6 ml, 41.6 mmol, 1 M in toluene) was added in a dropwise manner using a syringe pump (addition rate 1 mL/min) Upon complete addition the reaction was stirred at −78° C. for an additional 1 h 20 min. The reaction was quenched at −78° C. by addition of 10 mL of ethyl acetate followed by addition of 150 mL of a saturated aqueous solution of sodium potassium tartrate. Upon complete addition the cooling was removed, the reaction allowed to warm to room temperature and stirred at this temperature for 1 h. The mixture was diluted with ethyl acetate (200 mL) and filtered through a plug of celite using ethyl acetate for elution. The filtrate was transferred to a separation funnel and the organic layer was isolated. The aqueous phase was extracted with ethyl acetate (2×100 mL), the combined organics were washed with brine (100 mL), dried over MgSO₄, filtered, and concentrated under reduced pressure to afford an intermediate. The intermediate was used immediately in the subsequent step without further purification. Lithium chloride (2.20 g, 52.0 mmol) was placed in a round bottom flask, dried under vacuum with heating and allowed to cool to room temperature under vacuum. Acetonitrile (87 mL) was added followed by ethyl 2-(diethoxyphosphoryl)-2-fluoroacetate (5.79 g, 23.9 mmol). The solution was cooled to 0° C. using an ice/water bath and N,N-diisopropylethylamine (4.03 g, 5.5 ml, 31.2 mmol) was added. After 10 min stirring at this temperature a solution of the intermediate mentioned above in acetonitrile (33 ml) was added. Upon complete addition the cooling was removed and the reaction was stirred overnight at room temperature. The reaction mixture was concentrated to approximately 50 mL (under vacuum), ethyl acetate (250 mL), water (50 mL) and saturated aqueous NH₄Cl (50 mL) were added. The phases were separated and the aqueous layer was extracted with ethyl acetate (2×100 mL). The combined organics were dried over MgSO₄, filtered, and concentrated under reduced pressure. The crude material was purified using a CombiFlash system (220 g SiO$_2$, gradient elution; heptanes:ethyl acetate 100:0→60:40) to afford (R)-ethyl 5-((R)-1,1-dimethylethylsulfinamido)-2,4,4-trifluoro-5-(2-fluorophenyl)hex-2-enoate (5.1 g, 60% yield). $^1$H NMR (600 MHz, CDCl$_3$) δ 7.45 (tt, J=4.3, 2.2 Hz, 1H), 7.40-7.33 (m, 1H), 7.16 (tt, J=5.4, 2.7 Hz, 1H), 7.09 (ddd, J=13.2, 8.2, 1.2 Hz, 1H), 6.00 (dt, J=20.3, 14.5 Hz, 1H), 4.98 (d, J=4.1 Hz, 1H), 4.30 (q, J=7.1 Hz, 2H), 2.03 (s, 3H), 1.32 (t, J=7.2 Hz, 3H), 1.24 (s, 9H).

INTERMEDIATE: (6R)-3,5,5-trifluoro-6-(2-fluorophenyl)-6-methylpiperidin-2-one

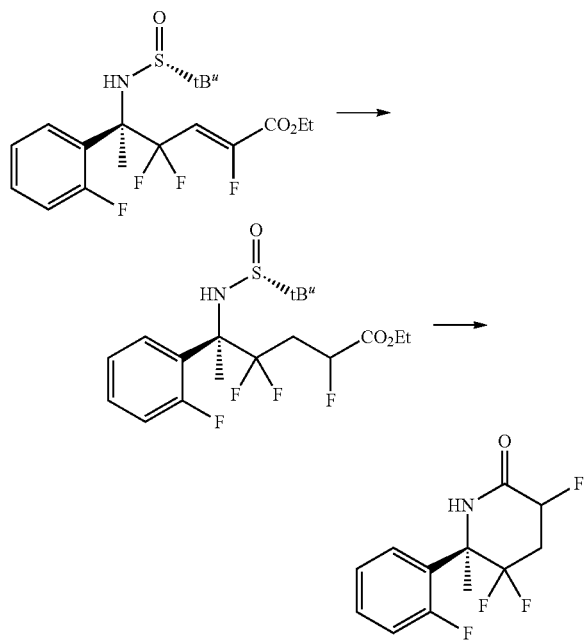

(R)-Ethyl 5-((R)-1,1-dimethylethylsulfinamido)-2,4,4-trifluoro-5-(2-fluorophenyl)hex-2-enoate (5.1 g, 12.5 mmol) was dissolved in ethyl acetate (200 mmol) and placed in a Parr-flask. Palladium on carbon (2.65 g, 2.49 mmol, 10%) was added and the Parr-flask was placed in a Parr-shaker (H$_2$-pressure=2.8 bar initially). After 16 h in the Parr shaker at room temperature the reaction mixture was filtered through a plug of celite using ethyl acetate for elution. The filtrate was concentrated under reduced pressure. This material was dissolved in ethyl acetate (200 ml, 3494 mmol) and the reaction mixture was split equally into two Parr-flasks. Palladium on carbon (2.65 g, 2.49 mmol, 10%) was split in two equal partitions and added to the two Parr-flasks. The flasks were placed in two different Parr-shakers (H$_2$-pressure=2.8 bar initially) and run in parallel. After 16 h in the Parr-shaker at room temperature the two suspensions were combined and filtered through a plug of celite using ethyl acetate for elution. The filtrate was concentrated under reduced pressure. The material thus obtained was dissolved in methanol (330 ml). HCl (4.7 ml, 19 mmol, 4 M in 1,4-dioxane) was added and the reaction was stirred at room temperature for 1 h 30 min. K$_2$CO$_3$ (5.16 g, 37.4 mmol) was added and the reaction was stirred at room temperature for another 1 h 30 min. The reaction was concentrated to dryness under reduced pressure and the residue was partitioned between water (200 mL) and ethyl acetate (250 mL). The phases were separated and the aqueous layer was extracted with ethyl acetate (2×100 mL). The combined organics were washed with brine, dried over MgSO$_4$, filtered, and concentrated under reduced pressure. The crude material was purified using a CombiFlash system (120 g SiO$_2$, gradient elution; heptanes:ethyl acetate 100:0→45:55) to afford (6R)-3,5,5-trifluoro-6-(2-fluorophenyl)-6-methylpiperidin-2-one (1.86 g, 57.2% yield) as a semi-solid/foam (1:1 mixture of diastereomers) LC-MS (m/z) 262.2 (MH$^+$) $t_R$=0.57 minutes (Method B).

INTERMEDIATE: (2R)-tert-butyl 3,3,5-trifluoro-2-(2-fluorophenyl)-2-methyl-6-oxopiperidine-1-carboxylate

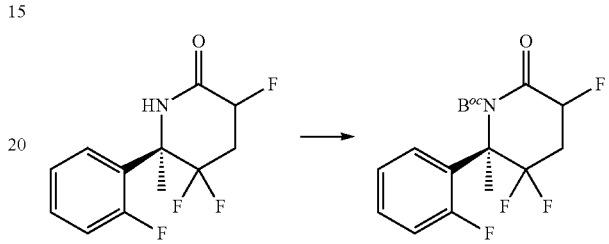

(6R)-3,5,5-Trifluoro-6-(2-fluorophenyl)-6-methylpiperidin-2-one (2.42 g, 9.26 mmol) (1:1 mixture of diastereomers) was placed in a round bottom flask. DMAP (0.283 g, 2.316 mmol) was added followed by a solution of di-tert-butyl dicarbonate (6.07 g, 27.8 mmol) in tetrahydrofuran (170 ml). The solution was stirred at room temperature for 1 h. The reaction was diluted with ethyl acetate (200 mL) and washed with a solution of water (50 mL) and saturated aqueous NH$_4$Cl (50 mL). The phases were separated and the aqueous layer was extracted with ethyl acetate (2×100 mL). The combined organics were washed with brine (50 mL), dried over MgSO$_4$, filtered, and concentrated under reduced pressure. The crude material was purified using a CombiFlash system (120 g SiO$_2$, gradient elution; heptanes:ethyl acetate 100:0→55:45) to afford (2R)-tert-butyl 3,3,5-trifluoro-2-(2-fluorophenyl)-2-methyl-6-oxopiperidine-1-carboxylate (2.60 g, 78% yield) (1:1 mixture of diastereomers).

INTERMEDIATE: (6R)-3,5,5-trifluoro-6-(2-fluorophenyl)-3,6-dimethylpiperidin-2-one

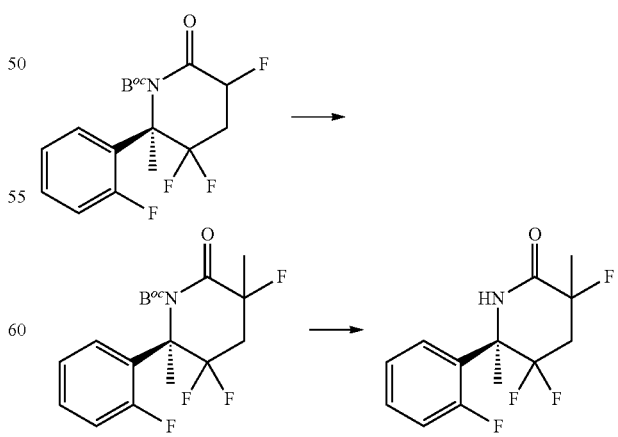

For the first step, two reactions were run in parallel under identical conditions with total amounts as described below.

(2R)-Tert-butyl 3,3,5-trifluoro-2-(2-fluorophenyl)-2-methyl-6-oxopiperidine-1-carboxylate (1.30 g, 3.60 mmol) (1:1 mixture of diastereomers) was dissolved in tetrahydrofuran (36 mL) (dried over 4 Å MS) and added to a dry round bottom flask. The solution was cooled to −78° C. using a dry ice/acetone bath. LiHMDS (lithium hexamethyldisilazide) (4.50 mL, 4.50 mmol, 1.0 M in tetrahydrofuran) was added in a dropwise manner and the resulting solution was stirred at stirred at −78° C. for 1 h. Methyl iodide (2.55 g, 1.13 mL, 18 mmol) was added in a dropwise manner and the solution was stirred at −78° C. for 45 min then the cooling was removed and the solution was stirred for another 15 min at room temperature. The solution was re-cooled to −78° C. and quenched with saturated aqueous NH$_4$Cl (25 mL). The cooling bath was removed and the reaction was allowed to warm to room temperature. The two reaction mixtures were combined and ethyl acetate (200 mL) and water (50 mL) were added. The phases were separated and the aqueous layer was extracted with ethyl acetate (2×100 mL). The combined organics were washed with brine, dried over MgSO$_4$, filtered, and concentrated under reduced pressure. All of the thus obtained material was dissolved in 1,2-dichloroethane (85 ml) and the solution was cooled to 0° C. using an ice/water bath. TFA (21 ml, 273 mmol) was added and the cooling bath was allowed to slowly expire overnight, with stirring of the reaction mixture. The reaction was diluted with toluene (50 mL) and concentrated to approximately 25 ml-under vacuum. The residue was diluted with ethyl acetate (150 mL) and washed with saturated aqueous NaHCO$_3$ (50 mL). The phases were separated and the aqueous layer was extracted with ethyl acetate (2×75 mL). The combined organics were washed with brine, dried over MgSO$_4$, filtered, and concentrated under reduced pressure. The crude material was purified using a CombiFlash system (80 g SiO$_2$, gradient elution; heptanes: ethyl acetate 100:0→50:50) to afford (6R)-3,5,5-trifluoro-6-(2-fluorophenyl)-3,6-dimethylpiperidin-2-one (1.86 g, 6.76 mmol, 94% yield) (1:1.8 mixture of diastereomers) LC-MS (m/z) 276.2 (MH$^+$) t$_R$=0.62 minutes (Method B).

INTERMEDIATE: (6R)-3,5,5-trifluoro-6-(2-fluoro-5-nitrophenyl)-3,6-dimethylpiperidin-2-one

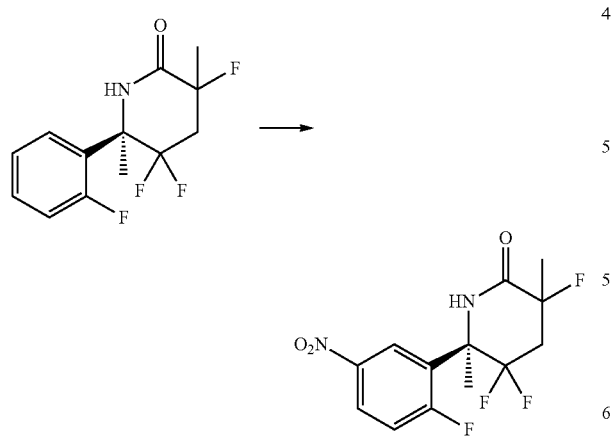

(6R)-3,5,5-Trifluoro-6-(2-fluorophenyl)-3,6-dimethylpiperidin-2-one (1.86 g, 6.76 mmol) (1:1.8 mixture of diastereomers) was suspended in trifluoroacteic acid (11.5 ml, 149 mmol). The mixture was cooled to 0° C. and concentrated H$_2$SO$_4$ (2.86 ml, 52.0 mmol, 97%) was added. Finally, fuming HNO$_3$ (0.33 ml, 7.4 mmol) was added in a dropwise manner and the reaction was stirred at 0° C. for 10 min. The reaction mixture was poured onto 150 g ice and basified to pH>11 using 5 M NaOH. The resulting suspension was extracted with ethyl acetate (250 mL). The phases were separated and the aqueous layer was extracted with ethyl acetate (2×100 mL). The combined organics were washed with a solution of saturated aqueous NH$_4$Cl (50 mL) and water (50 mL), dried over MgSO$_4$, filtered, and concentrated under reduced pressure to afford (6R)-3,5,5-trifluoro-6-(2-fluoro-5-nitrophenyl)-3,6-dimethylpiperidin-2-one (2.08 g, 6.50 mmol, 96% yield) (1:1.8 mixture of diastereomers) LC-MS (m/z) 321.1 (MH$^+$) t$_R$=0.62 minutes (Method B).

INTERMEDIATE: (6R)-6-(5-amino-2-fluorophenyl)-3,5,5-trifluoro-3,6-dimethylpiperidin-2-one

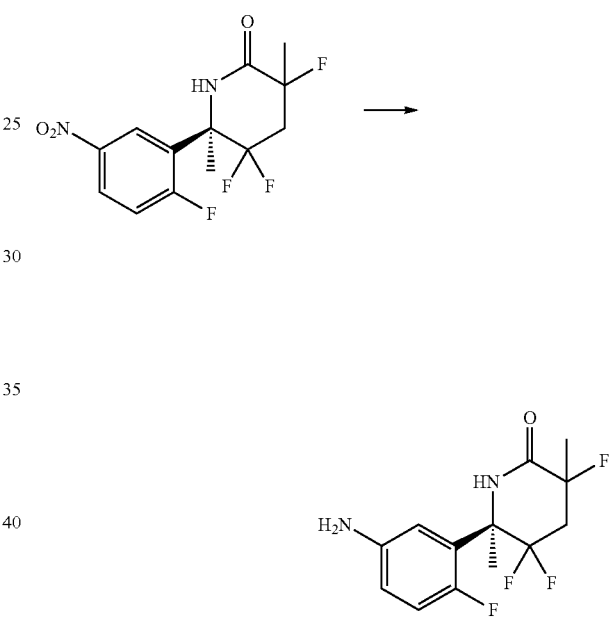

(6R)-3,5,5-Trifluoro-6-(2-fluoro-5-nitrophenyl)-3,6-dimethylpiperidin-2-one (2.08 g, 6.50 mmol) (1:1.8 mixture of diastereomers) was dissolved in methanol (28 ml). Ammonium formate (2.05 g, 32.5 mmol) was added followed by portionwise addition of palladium on carbon (1.38 g, 1.30 mmol, 10%). The reaction is slightly exothermic and the reaction mixture was briefly immersed into an ice/water bath to control the temperature increase. After the initial temperature increase had settled, the reaction was stirred at room temperature for another 10 min. The reaction was filtered through a plug of celite using methanol for elution. The filtrate was concentrated under reduced pressure and partitioned between ethyl acetate (100 mL) and saturated aqueous NaHCO$_3$ (50 mL). The phases were separated and the aqueous layer was extracted with ethyl acetate (2×50 mL). The combined organics were dried over MgSO$_4$, filtered and concentrated under reduced pressure to afford (6R)-6-(5-amino-2-fluorophenyl)-3,5,5-trifluoro-3,6-dimethylpiperidin-2-one (1.73 g, 5.96 mmol, 92% yield) (1:1.8 mixture of diastereomers). LC-MS Major: (m/z) 291.0 (MH$^+$-tert-butyl) t$_R$=0.40 minutes (Method B); Minor: (m/z) 291.0 (MH$^+$) t$_R$=0.41 min- INTERMEDIATE: tert-butyl (4-fluoro-3-((2R)-3,3,5-trifluoro-2,5-dimethyl-6-oxopiperidin-2-yl)-phenyl)carbamate

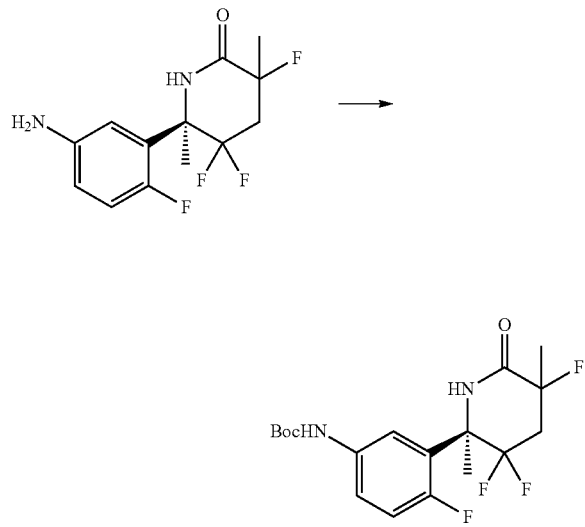

(6R)-6-(5-Amino-2-fluorophenyl)-3,5,5-trifluoro-3,6-dimethylpiperidin-2-one (1.73 g, 5.96 mmol) (1:1.8 mixture of diastereomers) was placed in a round bottom flask and a solution of di-tert-butyl dicarbonate (1.56 g, 7.15 mmol) in tetrahydrofuran (25 ml) (dried over 4 Å MS) was added. The solution was heated to 50° C. and stirred at this temperature overnight. The reaction was concentrated under reduced pressure and the crude material was purified using a CombiFlash system (80 g SiO$_2$, gradient elution; heptanes: ethyl acetate 100:0→50:50) to afford tert-butyl (4-fluoro-3-((2R)-3,3,5-trifluoro-2,5-dimethyl-6-oxopiperidin-2-yl)phenyl)carbamate (2.1 g, 5.38 mmol, 90% yield) (1:1.7 mixture of diastereomers) LC-MS Major: (m/z) 335.0 (MH$^+$-tert-butyl) $t_R$=0.74 minutes (Method B); Minor: (m/z) 391.2 (MH$^+$) $t_R$=0.76 minutes (Method B).

INTERMEDIATE: tert-butyl (4-fluoro-3-((2R,5S)-3,3,5-trifluoro-2,5-dimethyl-6-thioxopiperidin-2-yl)-phenyl)carbamate and tert-butyl (4-fluoro-3-((2R,5R)-3,3,5-trifluoro-2,5-dimethyl-6-thioxopiperidin-2-yl)phenyl)carbamate

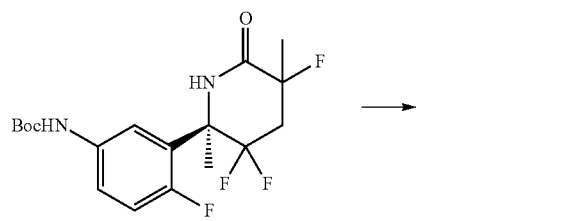

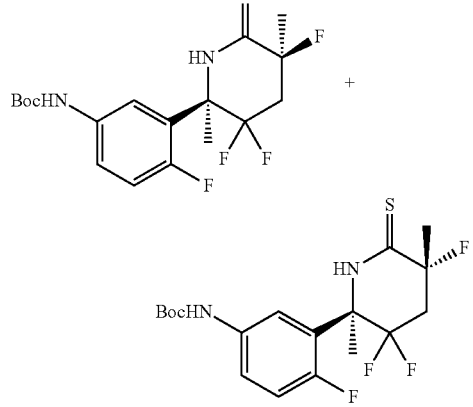

Tert-butyl (4-fluoro-3-((2R)-3,3,5-trifluoro-2,5-dimethyl-6-oxopiperidin-2-yl)phenyl)carbamate (2.1 g, 5.38 mmol) (1:1.7 mixture of diastereomers) was placed in a round bottom flask and dissolved in toluene (60 ml) (dried over 4 Å MS). Argon was bubbled through the reaction for 10 min followed by addition of Lawesson's reagent (2,4-bis(4-methoxyphenyl)-1,3,2,4-dithiadiphosphetane 2,4-disulfide) (2.18 g, 5.38 mmol). The reaction was carefully evacuated and backfilled with argon (×3). The suspension was heated to 80° C. The reaction was stirred at this temperature for 3 h 30 min. The reaction was allowed to cool to room temperature and concentrated under reduced pressure. The crude material was suspended in CHCl$_3$ and filtered. The filtrate was concentrated under reduced pressure and the crude material was purified using a CombiFlash system (120 g SiO$_2$, gradient elution; heptanes:ethyl acetate 100:0→80:20) to afford tert-butyl (4-fluoro-3-((2R,5S)-3,3,5-trifluoro-2,5-dimethyl-6-thioxopiperidin-2-yl)phenyl)carbamate (1.15 g, 52.6% yield) (fast eluting isomer) LC-MS (m/z) 407.4 (MH$^+$) $t_R$=0.83 minutes (Method B) and tert-butyl (4-fluoro-3-((2R,5R)-3,3,5-trifluoro-2,5-dimethyl-6-thioxopiperidin-2-yl)phenyl)carbamate (0.816 g (60% purity), 22.4% yield) (slow eluting isomer) LC-MS (m/z) 407.4 (MH$^+$) $t_R$=0.82 minutes (Method B).

INTERMEDIATE: (3S,6R)-6-(5-amino-2-fluorophenyl)-3,5,5-trifluoro-3,6-dimethylpiperidine-2-thione

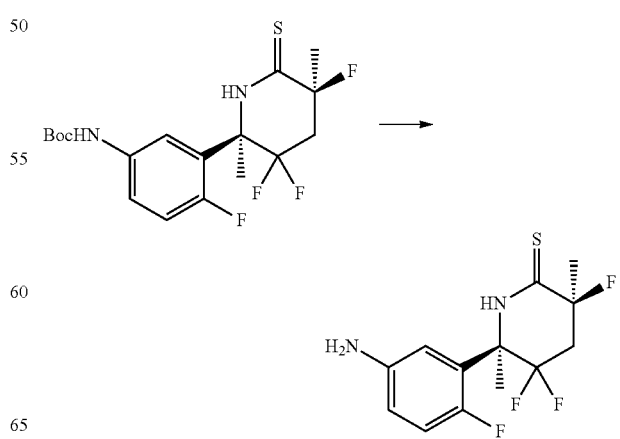

tert-butyl (4-fluoro-3-((2R,5S)-3,3,5-trifluoro-2,5-dimethyl-6-thioxopiperidin-2-yl)phenyl)carbamate (1.15 g, 2.83 mmol) was dissolved in dichloromethane (13 ml). The solution was cooled to 0° C. and TFA (6.5 ml, 84 mmol) was added. The solution was stirred at 0° C. for 1 h 20 min. The reaction was diluted with toluene (25 mL) and concentrated to approx 10 mL under reduced pressure. The residue was diluted with ethyl acetate (50 mL) and washed with saturated aqueous NaHCO$_3$ (25 mL). The phases were separated and the aqueous layer was extracted with ethyl acetate (2×25 mL). The combined organics were dried over MgSO$_4$, filtered, and concentrated under reduced pressure to afford (3S,6R)-6-(5-amino-2-fluorophenyl)-3,5,5-trifluoro-3,6-dimethylpiperidine-2-thione (548 mg (70% purity), 63.2% yield). The crude product was used in the next reaction step without further purification. LC-MS (m/z) 307.2 (MH$^+$) $t_R$=0.49 minutes (Method B) $^1$H NMR (600 MHz, CDCl$_3$) δ 7.93 (bs, 1H), 6.93-6.88 (m, 1H), 6.66-6.61 (m, 1H), 6.59-6.55 (m, 1H), 2.62-2.57 (m, 2H), 1.90 (s, 3H), 1.86 (d, J=22.4 Hz, 3H) $[α]_D^{20}$=−211° (589 nm, c=0.1 g/100 mL, MeOH INTERMEDIATE: (3R,6R)-6-(5-amino-2-fluorophenyl)-3,5,5-trifluoro-3,6-dimethylpiperidine-2-thione

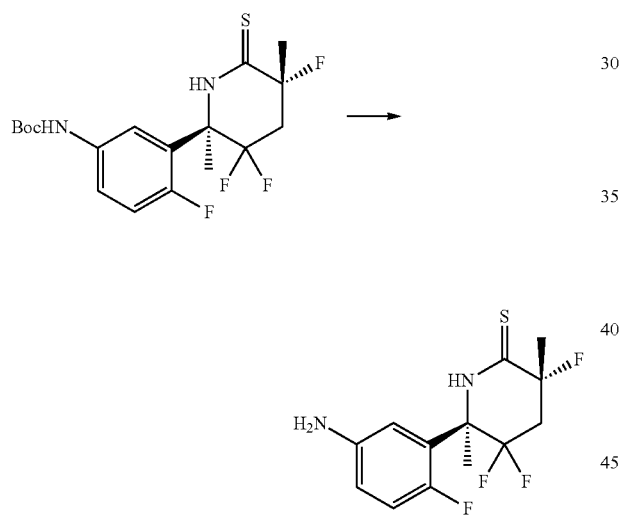

tert-butyl (4-fluoro-3-((2R,5R)-3,3,5-trifluoro-2,5-dimethyl-6-thioxopiperidin-2-yl)phenyl)carbamate (816 mg, 2.01 mmol) was dissolved in dichloromethane (9.2 mL). The solution was cooled to 0° C. and TFA (4.6 mL, 59.5 mmol) was added. The solution was stirred at 0° C. for 1 h 20 min. The reaction was diluted with toluene (15 mL) and concentrated to approx. 10 mL under reduced pressure. The residue was diluted with ethyl acetate (50 mL) and washed with saturated aqueous NaHCO$_3$ (25 mL). The phases were separated and the aqueous layer was extracted with ethyl acetate (2×25 mL). The combined organics were dried over MgSO$_4$, filtered, and concentrated under reduced pressure to afford (3R,6R)-6-(5-amino-2-fluorophenyl)-3,5,5-trifluoro-3,6-dimethylpiperidine-2-thione (587 mg, (50% purity), 47.7% yield). The material was used in the next reaction step without further purification.

LC-MS (m/z) 307.0 (MH$^+$) $t_R$=0.47 minutes (Method A) $^1$H NMR (600 MHz, CDCl$_3$) δ 8.18 (bs, 1H), 6.92 (dd, J=12.0, 8.7 Hz, 1H), 6.69-6.63 (m, 1H), 6.52-6.45 (m, 1H), 2.78-2.66 (m, 1H), 2.56-2.43 (m, 1H), 1.91 (s, 3H), 1.79 (dd, J=20.3, 12.5 Hz, 3H).

INTERMEDIATE: 5-(Methoxy-d$_3$) picolinic acid

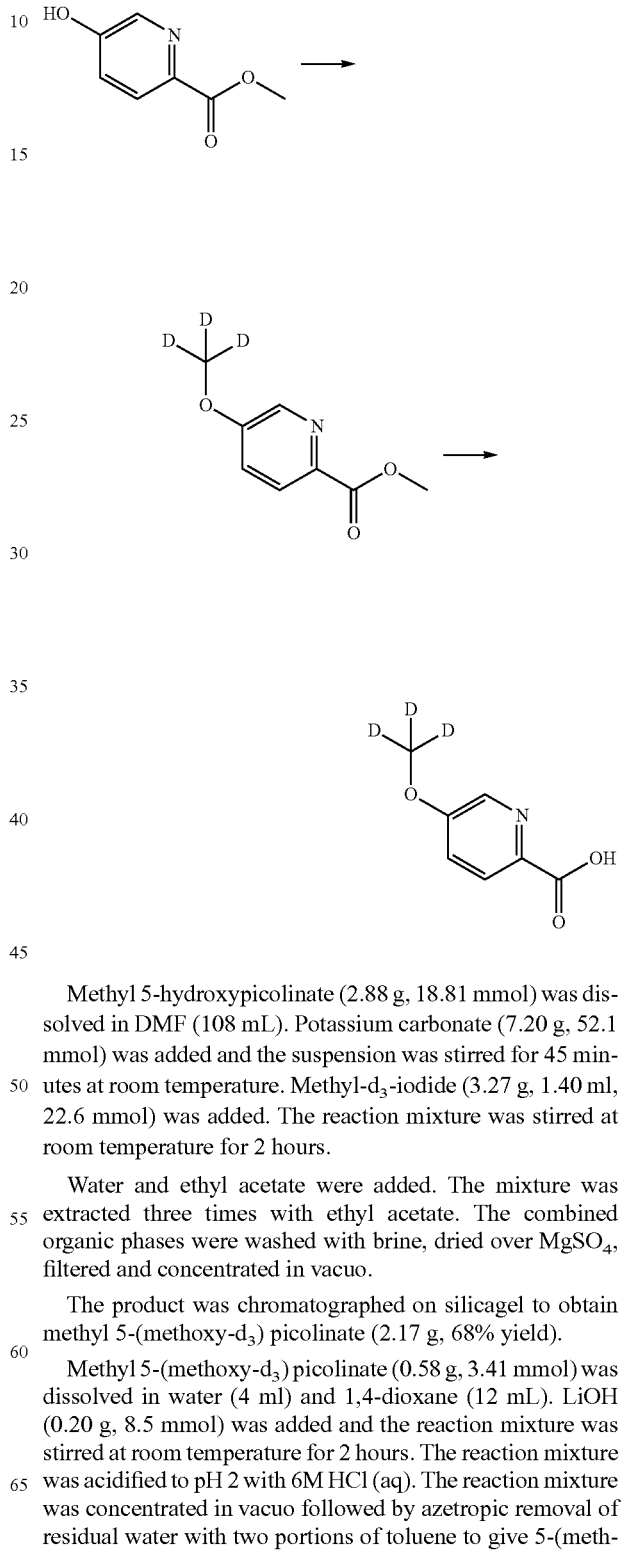

Methyl 5-hydroxypicolinate (2.88 g, 18.81 mmol) was dissolved in DMF (108 mL). Potassium carbonate (7.20 g, 52.1 mmol) was added and the suspension was stirred for 45 minutes at room temperature. Methyl-d$_3$-iodide (3.27 g, 1.40 ml, 22.6 mmol) was added. The reaction mixture was stirred at room temperature for 2 hours.

Water and ethyl acetate were added. The mixture was extracted three times with ethyl acetate. The combined organic phases were washed with brine, dried over MgSO$_4$, filtered and concentrated in vacuo.

The product was chromatographed on silicagel to obtain methyl 5-(methoxy-d$_3$) picolinate (2.17 g, 68% yield).

Methyl 5-(methoxy-d$_3$) picolinate (0.58 g, 3.41 mmol) was dissolved in water (4 ml) and 1,4-dioxane (12 mL). LiOH (0.20 g, 8.5 mmol) was added and the reaction mixture was stirred at room temperature for 2 hours. The reaction mixture was acidified to pH 2 with 6M HCl (aq). The reaction mixture was concentrated in vacuo followed by azeotropic removal of residual water with two portions of toluene to give 5-(methoxy-d₃) picolinic acid. Used in next step without further purification. LC-MS (m/z) 157.1 (MH⁺) $t_R$=0.19 minutes (Method A)

Preparation of the Compounds of the Invention

Example 1

N-(3-((2R,5S)-6-amino-3,3,5-trifluoro-2,5-dimethyl-2,3,4,5-tetrahydropyridin-2-yl)-4-fluorophenyl)-5-fluoropicolinamide

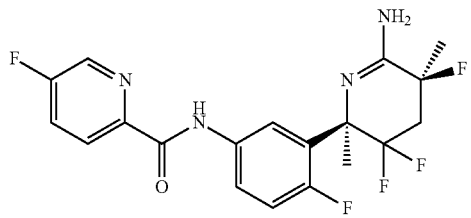 [SMILES: C[C@]1(F)CC(F)(F)[C@@](C)(c2cc(NC(=O)c3ccc(F)cn3)ccc2F)N=C1N]

5-fluoropicolinic acid (269 mg, 1.906 mmol) and 1-[bis(dimethylamino)methylene]-1H-1,2,3-triazolo-[4,5-b]pyridinium 3-oxid hexafluorophosphate (HATU) (797 mg, 2.10 mmol) were placed in a round bottom flask, dissolved in DMF (5.2 mL), and stirred at room temperature for 5 min. (3S,6R)-6-(5-amino-2-fluorophenyl)-3,5,5-trifluoro-3,6-dimethylpiperidine-2-thione (292 mg, 0.953 mmol) was added followed by N,N-diisopropylethylamine (830 µl, 4.77 mmol) and the reaction was stirred at room temperature for 5 min. The reaction was diluted with ethyl acetate (50 mL) and washed with a mixture of water (25 mL) and saturated aqueous NH₄Cl (25 mL). The phases were separated and the aqueous layer was extracted with ethyl acetate (2×50 mL). The combined organics were dried over MgSO₄, filtered, and concentrated under reduced pressure. The intermediate 5-fluoro-N-(4-fluoro-3-((2R,5S)-3,3,5-trifluoro-2,5-dimethyl-6-thioxopiperidin-2-yl)phenyl)picolinamide was purified using a CombiFlash system (40 g SiO₂, gradient elution; heptanes:ethyl acetate 100:0→60:40). The intermediate (225 mg, 0.523 mmol) was split in two equal portions and placed in two separate reaction vials. Ammonia (14.6 mL, 102 mmol, 7 M in methanol) was also split in two equal portions and added to the two vials. The vials were capped and heated to 65° C. using an oil bath. After 6 h stirring at this temperature the reactions were allowed to cool to room temperature, the mixtures were combined and concentrated under reduced pressure. The crude material was subjected to silica-gel chromatography (eluent; heptane:ethyl acetate=50:50→0:100) to afford N-(3-((2R,5S)-6-amino-3,3,5-trifluoro-2,5-dimethyl-2,3,4,5-tetrahydropyridin-2-yl)-4-fluorophenyl)-5-fluoropico linamide (124 mg, 57% yield).

LC-MS (m/z) 413.2 (MH+); $t_R$=0.54 (Method A) ¹H NMR (600 MHz, CDCl₃) δ 9.78 (br s, 1H), 8.45 (d, J=2.7 Hz, 1H), 8.33 (dd, J=8.7, 4.6 Hz, 1H), 7.89 (ddd, J=8.8, 3.8, 2.9 Hz, 1H), 7.59 (ddd, J=8.6, 8.0, 2.8 Hz, 1H), 7.57 (dd, J=6.8, 2.7 Hz, 1H), 7.09 (dd, J=11.8, 8.8 Hz, 1H), 4.74 (br s, 2H), 2.60-2.37 (m, 2H), 1.79 (t, J=2.8 Hz, 3H), 1.76 (d, J=23.6 Hz, 3H).

The following compounds were prepared in a way similar to example 1:

Example 2

N-(3-((2R,5R)-6-amino-3,3,5-trifluoro-2,5-dimethyl-2,3,4,5-tetrahydropyridin-2-yl)-4-fluorophenyl)-5-fluoropicolinamide

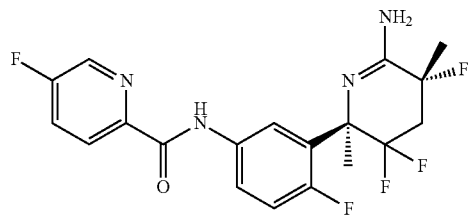 [SMILES: C[C@@]1(F)CC(F)(F)[C@@](C)(c2cc(NC(=O)c3ccc(F)cn3)ccc2F)N=C1N]

Prepared from (3R,6R)-6-(5-amino-2-fluorophenyl)-3,5,5-trifluoro-3,6-dimethylpiperidine-2-thione and 5-fluoropicolinic acid LC-MS (m/z) 413.1 (MH⁺) $t_R$=0.55 minutes (Method A) ¹H NMR (600 MHz, CDCl₃) δ 9.78 (br s, 1H), 8.45 (d, J=2.8 Hz, 1H), 8.34-8.31 (m, 1H), 7.84 (ddd, J=8.8, 3.8, 2.9 Hz, 1H), 7.61-7.57 (m, 2H), 7.08 (dd, J=11.6, 8.8 Hz, 1H), 4.69 (br s, 2H), 2.75-2.62 (m, 1H), 2.47-2.40 (m, 1H), 1.82 (s, 3H), 1.75 (d, J=23.9 Hz, 3H)

Example 3

N-(3-((2R,5S)-6-amino-3,3,5-trifluoro-2,5-dimethyl-2,3,4,5-tetrahydropyridin-2-yl)-4-fluorophenyl)-5-chloropicolinamide

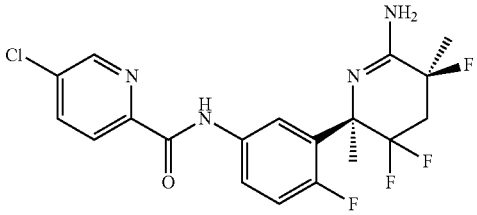 [SMILES: C[C@]1(F)CC(F)(F)[C@@](C)(c2cc(NC(=O)c3ccc(Cl)cn3)ccc2F)N=C1N]

Prepared from (3S,6R)-6-(5-amino-2-fluorophenyl)-3,5,5-trifluoro-3,6-dimethylpiperidine-2-thione and 5-chloropicolinic acid LC-MS (m/z) 429.2 (MH⁺) $t_R$=0.57 minutes (Method A) ¹H NMR (600 MHz, CDCl₃) δ 9.81 (br s, 1H), 8.56 (dd, J=2.4, 0.7 Hz, 1H), 8.24 (dd, J=8.4, 0.7 Hz, 1H), 7.91-7.85

(m, 2H), 7.59 (dd, J=6.9, 2.7 Hz, 1H), 7.09 (dd, J=11.8, 8.8 Hz, 1H), 2.61-2.35 (m, 2H), 1.80 (t, J=2.8 Hz, 3H), 1.76 (d, J=23.6 Hz, 3H)

Example 4

N-(3-((2R,5S)-6-amino-3,3,5-trifluoro-2,5-dimethyl-2,3,4,5-tetrahydropyridin-2-yl)-4-fluorophenyl)-5-cyanopicolinamide

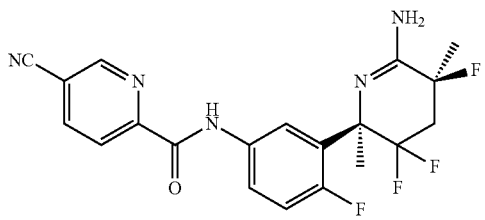 [SMILES: C[C@]1(F)CC(F)(F)[C@@](C)(c2cc(NC(=O)c3ccc(C#N)cn3)ccc2F)N=C1N]

Prepared from (3S,6R)-6-(5-amino-2-fluorophenyl)-3,5,5-trifluoro-3,6-dimethylpiperidine-2-thione and 5-cyanopicolinic acid LC-MS (m/z) 420.0 (MH$^+$) t$_R$=1.79 minutes (Method B)
$^1$H NMR (600 MHz, DMSO-d$_6$) δ 10.82 (br s, 1H), 9.20 (dd, J=2.0, 0.8 Hz, 1H), 8.58 (dd, J=8.1, 2.0 Hz, 1H), 8.28 (dd, J=8.2, 0.7 Hz, 1H), 7.94 (dd, J=7.2, 2.7 Hz, 1H), 7.89-7.83 (m, 1H), 7.15 (dd, J=11.9, 8.8 Hz, 1H), 6.22 (br s, 2H), 2.74-2.59 (m, 1H), 2.49-2.38 (m, 1H), 1.67 (d, J=22.7 Hz, 3H), 1.62 (s, 3H)

Example 5

N-(3-((2R,5S)-6-amino-3,3,5-trifluoro-2,5-dimethyl-2,3,4,5-tetrahydropyridin-2-yl)-4-fluorophenyl)-5-methoxypyrazine-2-carboxamide

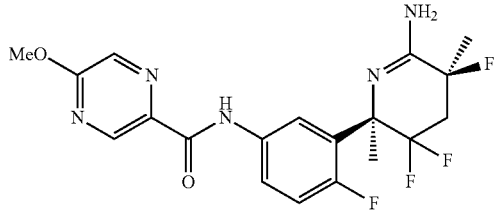 [SMILES: COc1cnc(C(=O)Nc2ccc(F)c([C@@]3(C)N=C(N)[C@@](C)(F)CC3(F)F)c2)cn1]

Prepared from (3S,6R)-6-(5-amino-2-fluorophenyl)-3,5,5-trifluoro-3,6-dimethylpiperidine-2-thione and 5-methoxypyrazine-2-carboxylic acid LC-MS (m/z) 426.3 (MH$^+$) t$_R$=0.51 minutes (Method A)
$^1$H NMR (600 MHz, CDCl$_3$) δ 9.50 (br s, 1H), 9.00 (d, J=1.3 Hz, 1H), 8.13 (d, J=1.3 Hz, 1H), 7.88 (ddd, J=8.8, 3.8, 2.9 Hz, 1H), 7.58 (dd, J=6.8, 2.7 Hz, 1H), 7.08 (dd, J=11.8, 8.8 Hz, 1H), 4.80 (br s, 2H), 4.06 (s, 3H), 2.59-2.35 (m, 2H), 1.79 (t, J=2.8 Hz, 3H), 1.75 (d, J=23.6 Hz, 3H)

Example 6

N-(3-((2R,5S)-6-amino-3,3,5-trifluoro-2,5-dimethyl-2,3,4,5-tetrahydropyridin-2-yl)-4-fluorophenyl)-1-(difluoromethyl)-1H-pyrazole-3-carboxamide

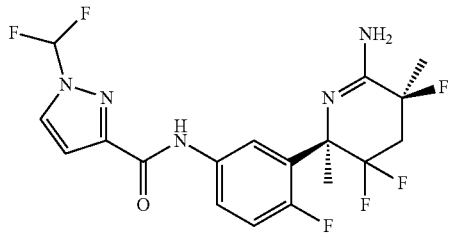 [SMILES: C[C@]1(F)CC(F)(F)[C@@](C)(c2cc(NC(=O)c3ccn(C(F)F)n3)ccc2F)N=C1N]

Prepared from (3S,6R)-6-(5-amino-2-fluorophenyl)-3,5,5-trifluoro-3,6-dimethylpiperidine-2-thione and 1-(difluoromethyl)-1H-pyrazole-3-carboxylic acid LC-MS (m/z) 434.2 (MH$^+$) t$_R$=0.49 minutes (Method A)
$^1$H NMR (600 MHz, CDCl$_3$) δ 8.66 (br s, 1H), 7.86 (d, J=2.7 Hz, 1H), 7.78 (ddd, J=8.8, 3.7, 2.9 Hz, 1H), 7.58 (dd, J=6.8, 2.7 Hz, 1H), 7.18 (t, J=60.3 Hz, 1H), 7.07 (dd, J=11.7, 8.8 Hz, 1H), 7.03 (d, J=2.7 Hz, 1H), 4.57 (br s, 2H), 2.59-2.34 (m, 2H), 1.80 (t, J=2.8 Hz, 3H), 1.74 (d, J=23.6 Hz, 3H)

Example 7

N-(3-((2R,5S)-6-amino-3,3,5-trifluoro-2,5-dimethyl-2,3,4,5-tetrahydropyridin-2-yl)-4-fluorophenyl)-2-methyloxazole-4-carboxamide

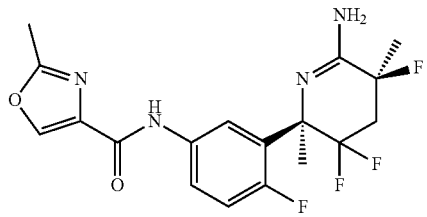 [SMILES: Cc1nc(C(=O)Nc2ccc(F)c([C@@]3(C)N=C(N)[C@@](C)(F)CC3(F)F)c2)co1]

Prepared from (3S,6R)-6-(5-amino-2-fluorophenyl)-3,5,5-trifluoro-3,6-dimethylpiperidine-2-thione and 2-methyloxazole-4-carboxylic acid LC-MS (m/z) 399 (MH$^+$) t$_R$=0.46 minutes (Method A) $^1$H NMR (600 MHz, DMSO-d$_6$) δ 10.12 (br s, 1H), 8.62 (s, 1H), 7.82 (dd, J=7.1, 2.5 Hz, 1H), 7.75 (dt, J=8.5, 3.2 Hz, 1H), 7.09

(dd, J=11.9, 8.8 Hz, 1H), 6.19 (br s, 2H), 2.71-2.57 (m, 1H), 2.51 (s, 3H), 2.47-2.35 (m, 1H), 1.66 (d, J=22.8 Hz, 3H), 1.61 (s, 3H)

Example 8

N-(3-((2R,5S)-6-amino-3,3,5-trifluoro-2,5-dimethyl-2,3,4,5-tetrahydropyridin-2-yl)-4-fluorophenyl) thiazole-2-carboxamide

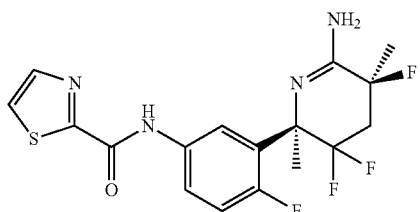

Prepared from (3S,6R)-6-(5-amino-2-fluorophenyl)-3,5,5-trifluoro-3,6-dimethylpiperidine-2-thione and thiazole-2-carboxylic acid LC-MS (m/z) 401 (MH$^+$) $t_R$=0.49 minutes (Method A) $^1$H NMR (600 MHz, DMSO-d$_6$) δ 10.83 (br s, 1H), 8.13 (d, J=3.1 Hz, 1H), 8.10 (d, J=3.1 Hz, 1H), 7.97 (dd, J=7.2, 2.7 Hz, 1H), 7.78 (dt, J=8.7, 3.4 Hz, 1H), 7.14 (dd, J=11.9, 8.8 Hz, 1H), 6.22 (br s, 2H), 2.73-2.59 (m, 1H), 2.49-2.37 (m, 1H), 1.68 (d, J=22.7 Hz, 3H), 1.63 (s, 3H)

Example 9

N-(3-((2R,5S)-6-amino-3,3,5-trifluoro-2,5-dimethyl-2,3,4,5-tetrahydropyridin-2-yl)-4-fluorophenyl)-4-bromo-1-methyl-1H-imidazole-2-carboxamide

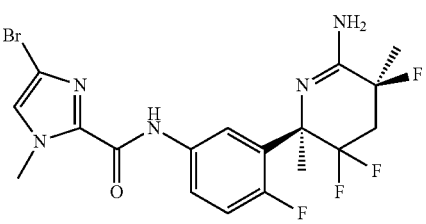 [SMILES: Cn1cc(Br)nc1C(=O)Nc1ccc(F)c([C@@]2(C)N=C(N)[C@@](C)(F)CC2(F)F)c1]

Prepared from (3S,6R)-6-(5-amino-2-fluorophenyl)-3,5,5-trifluoro-3,6-dimethylpiperidine-2-thione and 4-bromo-1-methyl-1H-imidazole-2-carboxylic acid LC-MS (m/z) 475.9 (MH$^+$) $t_R$=0.55 minutes (Method A) $^1$H NMR (600 MHz, DMSO-d$_6$) δ 10.42 (br s, 1H), 7.83 (dd, J=7.2, 2.7 Hz, 1H), 7.76-7.72 (m, 1H), 7.63 (s, 1H), 7.09 (dd, J=11.9, 8.8 Hz, 1H), 6.20 (br s, 2H), 3.96 (s, 3H), 2.72-2.58 (m, 1H), 2.49-2.36 (m, 1H), 1.67 (d, J=22.7 Hz, 3H), 1.61 (s, 3H)

Example 10

N-(3-((2R,5S)-6-amino-3,3,5-trifluoro-2,5-dimethyl-2,3,4,5-tetrahydropyridin-2-yl)-4-fluorophenyl)-4-methylthiazole-2-carboxamide

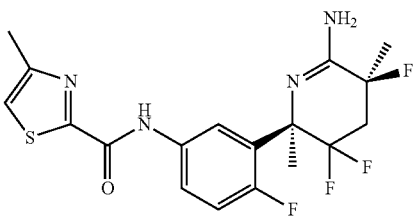 [SMILES: Cc1csc(C(=O)Nc2ccc(F)c([C@@]3(C)N=C(N)[C@@](C)(F)CC3(F)F)c2)n1]

Prepared from (3S,6R)-6-(5-amino-2-fluorophenyl)-3,5,5-trifluoro-3,6-dimethylpiperidine-2-thione and 4-methylthiazole-2-carboxylic acid LC-MS (m/z) 415 (MH$^+$) $t_R$=0.53 minutes (Method A) $^1$H NMR (600 MHz, DMSO-d$_6$) δ 10.74 (br s, 1H), 7.95 (dd, J=7.2, 2.7 Hz, 1H), 7.78 (dt, J=8.7, 3.4 Hz, 1H), 7.68 (d, J=0.8 Hz, 1H), 7.12 (dd, J=11.9, 8.8 Hz, 1H), 6.22 (br s, 2H), 2.72-2.59 (m, 1H), 2.50 (s, 3H), 2.49-2.36 (m, 1H), 1.67 (d, J=22.8 Hz, 3H), 1.62 (s, 3H)

Example 11

N-(3-((2R,5S)-6-amino-3,3,5-trifluoro-2,5-dimethyl-2,3,4,5-tetrahydropyridin-2-yl)-4-fluorophenyl)-5-(trifluoromethyl)picolinamide

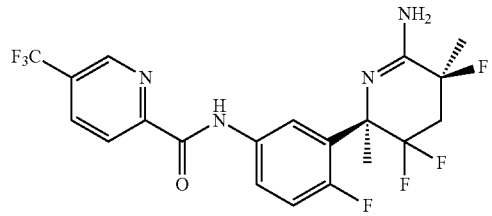 [SMILES: C[C@]1(F)CC(F)(F)[C@@](C)(c2cc(NC(=O)c3ccc(C(F)(F)F)cn3)ccc2F)N=C1N]

Prepared from (3S,6R)-6-(5-amino-2-fluorophenyl)-3,5,5-trifluoro-3,6-dimethylpiperidine-2-thione and 5-(trifluoromethyl)picolinic acid LC-MS (m/z) 463 (MH$^+$) $t_R$=0.61 minutes (Method A) $^1$H NMR (600 MHz, DMSO-d$_6$) δ 10.81 (br s, 1H), 9.13-9.11 (m, 1H), 8.49 (dd, J=8.3, 2.1 Hz, 1H), 8.34 (d, J=8.2 Hz, 1H), 7.95 (dd, J=7.1, 2.7 Hz, 1H), 7.90 (dt, J=8.7, 3.4 Hz, 1H), 7.16 (dd, J=11.9, 8.8 Hz, 1H), 6.25 (br s, 2H), 2.74-2.61 (m, 1H), 2.51-2.38 (m, 1H), 1.69 (d, J=22.7 Hz, 3H), 1.64 (s, 3H)

Example 12

N-(3-((2R,5S)-6-amino-3,3,5-trifluoro-2,5-dimethyl-2,3,4,5-tetrahydropyridin-2-yl)-4-fluorophenyl)-5-methoxypyrimidine-2-carboxamide

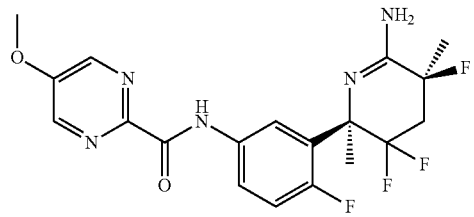 [SMILES: COc1cnc(C(=O)Nc2ccc(F)c([C@@]3(C)N=C(N)[C@@](C)(F)CC3(F)F)c2)nc1]

Prepared from (3S,6R)-6-(5-amino-2-fluorophenyl)-3,5,5-trifluoro-3,6-dimethylpiperidine-2-thione and 5-methoxypyrimidine-2-carboxylic acid (Prepared as described in Scott, Jack D. et al. PCT Int. Appl. 2011044181)

LC-MS (m/z) 426 (MH$^+$) t$_R$=0.45 minutes (Method A) $^1$H NMR (600 MHz, DMSO-d$_6$) δ 10.60 (br s, 1H), 8.72 (s, 2H), 7.90-7.86 (m, 1H), 7.83 (dd, J=7.1, 2.7 Hz, 1H), 7.14 (dd, J=11.9, 8.8 Hz, 1H), 6.23 (br s, 2H), 4.02 (s, 3H), 2.74-2.59 (m, 1H), 2.49-2.37 (m, 1H), 1.67 (d, J=22.7 Hz, 3H), 1.63 (s, 3H)

Example 13

N-(3-((2R,5S)-6-amino-3,3,5-trifluoro-2,5-dimethyl-2,3,4,5-tetrahydropyridin-2-yl)-4-fluorophenyl)-2-(difluoromethyl)oxazole-4-carboxamide

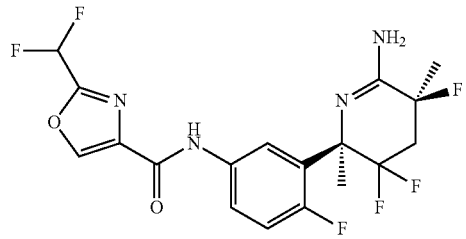 [SMILES: C[C@]1(F)CC(F)(F)[C@@](C)(c2cc(NC(=O)c3coc(C(F)F)n3)ccc2F)N=C1N]

Prepared from (3S,6R)-6-(5-amino-2-fluorophenyl)-3,5,5-trifluoro-3,6-dimethylpiperidine-2-thione and 2-(difluoromethyl)oxazole-4-carboxylic acid LC-MS (m/z) 435 (MH$^+$) t$_R$=0.51 minutes (Method A) $^1$H NMR (600 MHz, DMSO-d$_6$) δ 10.42 (br s, 1H), 9.01 (s, 1H), 7.81 (dd, J=7.1, 2.7 Hz, 1H), 7.76 (dt, J=8.5, 3.3 Hz, 1H), 7.33 (t, J=51.9 Hz, 1H), 7.12 (dd, J=11.9, 8.8 Hz, 1H), 6.20 (br s, 2H), 2.74-2.58 (m, 1H), 2.48-2.36 (m, 1H), 1.67 (d, J=22.7 Hz, 3H), 1.62 (s, 3H)

Example 14

N-(3-((2R,5S)-6-amino-3,3,5-trifluoro-2,5-dimethyl-2,3,4,5-tetrahydropyridin-2-yl)-4-fluorophenyl)-4-(fluoromethyl)oxazole-2-carboxamide

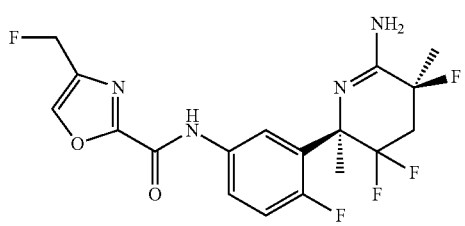 [SMILES: C[C@]1(F)CC(F)(F)[C@@](C)(c2cc(NC(=O)c3nc(CF)co3)ccc2F)N=C1N]

Prepared from (3S,6R)-6-(5-amino-2-fluorophenyl)-3,5,5-trifluoro-3,6-dimethylpiperidine-2-thione and 4-(fluoromethyl)oxazole-2-carboxylic acid LC-MS (m/z) 417 (MH$^+$) t$_R$=0.46 minutes (Method A) $^1$H NMR (600 MHz, DMSO-d$_6$) δ 11.04 (br s, 1H), 8.56 (d, J=5.0 Hz, 1H), 7.88 (dd, J=7.2, 2.7 Hz, 1H), 7.80-7.75 (m, 1H), 7.14 (dd, J=11.9, 8.8 Hz, 1H), 6.21 (br s, 2H), 5.43 (d, J=48.0 Hz, 2H), 2.74-2.58 (m, 1H), 2.48-2.35 (m, 1H), 1.67 (d, J=22.8 Hz, 3H), 1.62 (s, 3H)

Example 15

N-(3-((2R,5S)-6-amino-3,3,5-trifluoro-2,5-dimethyl-2,3,4,5-tetrahydropyridin-2-yl)-4-fluorophenyl)-4-(fluoromethyl)thiazole-2-carboxamide

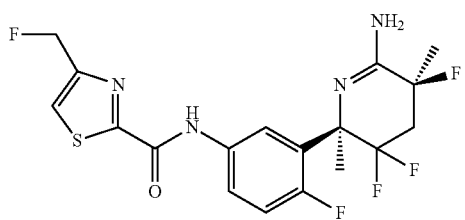

Prepared from (3S,6R)-6-(5-amino-2-fluorophenyl)-3,5,5-trifluoro-3,6-dimethylpiperidine-2-thione and 4-(fluoromethyl)thiazole-2-carboxylic acid LC-MS (m/z) 433 (MH$^+$) t$_R$=0.52 minutes (Method A) $^1$H NMR (600 MHz, DMSO-d$_6$) δ 10.90 (br s, 1H), 8.25 (d, J=3.2 Hz, 1H), 7.94 (dt, J=11.2, 5.6 Hz, 1H), 7.81-7.73 (m, 1H), 7.13 (dd, J=11.9, 8.8 Hz, 1H), 6.21 (br s, 2H), 5.57 (d, J=47.7 Hz, 2H), 2.72-2.57 (m, 1H), 2.48-2.36 (m, 1H), 1.67 (d, J=22.8 Hz, 3H), 1.62 (s, 3H)

Example 16

N-(3-((2R,5S)-6-amino-3,3,5-trifluoro-2,5-dimethyl-2,3,4,5-tetrahydropyridin-2-yl)-4-fluorophenyl)-5-(difluoromethyl)pyrazine-2-carboxamide

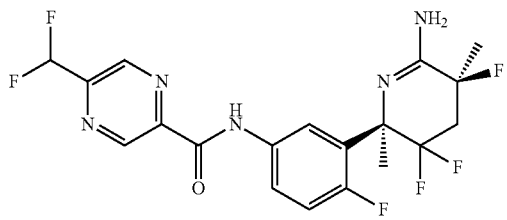 [SMILES: C[C@]1(F)CC(F)(F)[C@@](C)(c2cc(NC(=O)c3cnc(C(F)F)cn3)ccc2F)N=C1N]

Prepared from (3S,6R)-6-(5-amino-2-fluorophenyl)-3,5,5-trifluoro-3,6-dimethylpiperidine-2-thione and 5-(difluoromethyl)pyrazine-2-carboxylic acid LC-MS (m/z) 446 (MH+) $t_R$=0.52 minutes (Method A) $^1$H NMR (600 MHz, CDCl$_3$) δ 9.63 (br s, 1H), 9.53 (s, 1H), 8.92 (s, 1H), 7.90-7.86 (m, 1H), 7.63 (dd, J=6.8, 2.7 Hz, 1H), 7.11 (dd, J=11.6, 8.8 Hz, 1H), 6.80 (t, J=54.5 Hz, 1H), 4.76 (br s, 2H), 2.64-2.34 (m, 2H), 1.80 (t, J=2.7 Hz, 3H), 1.77 (d, J=23.5 Hz, 3H)

Example 17

N-(3-((2R,5S)-6-amino-3,3,5-trifluoro-2,5-dimethyl-2,3,4,5-tetrahydropyridin-2-yl)-4-fluorophenyl)-5-methoxypicolinamide

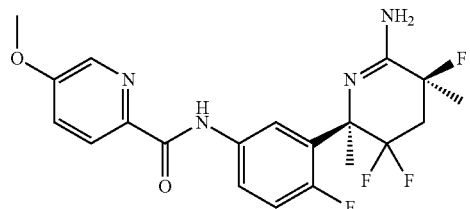

Prepared from (3S,6R)-6-(5-amino-2-fluorophenyl)-3,5,5-trifluoro-3,6-dimethylpiperidine-2-thione and 5-methoxypicolinic acid LC-MS (m/z) 425 (MH+) $t_R$=0.52 minutes (Method A) $^1$H NMR (600 MHz, DMSO-d$_6$) δ 10.42 (br s, 1H), 8.39 (dd, J=2.9, 0.4 Hz, 1H), 8.13-8.11 (m, 1H), 7.91-7.85 (m, 2H), 7.61 (dd, J=8.8, 2.9 Hz, 1H), 7.16-7.09 (m, 1H), 6.27 (br s, 2H), 3.93 (s, J=2.9 Hz, 3H), 2.73-2.59 (m, 1H), 2.49-2.38 (m, 1H), 1.68 (d, J=22.7 Hz, 3H), 1.63 (s, 3H)

Example 18

N-(3-((2R,5S)-6-amino-3,3,5-trifluoro-2,5-dimethyl-2,3,4,5-tetrahydropyridin-2-yl)-4-fluorophenyl)-5-cyano-3-methylpicolinamide

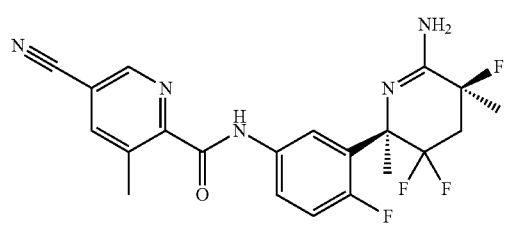 [SMILES: Cc1cc(C#N)cnc1C(=O)Nc1ccc(F)c([C@@]2(C)N=C(N)[C@@](C)(F)CC2(F)F)c1]

Prepared from (3S,6R)-6-(5-amino-2-fluorophenyl)-3,5,5-trifluoro-3,6-dimethylpiperidine-2-thione and 5-cyano-3-methylpicolinic acid (Prepared as described in Badiger, Sangamesh et al. PCT Int. Appl., 2012095469)

LC-MS (m/z) 434 (MH+) $t_R$=0.53 minutes (Method A).

Example 19

N-(3-((2R,5S)-6-amino-3,3,5-trifluoro-2,5-dimethyl-2,3,4,5-tetrahydropyridin-2-yl)-4-fluorophenyl)-5-methoxy-3-methylpyrazine-2-carboxamide

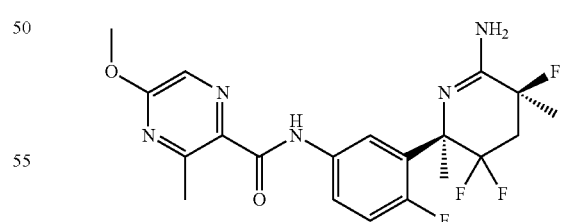

Prepared from (3S,6R)-6-(5-amino-2-fluorophenyl)-3,5,5-trifluoro-3,6-dimethylpiperidine-2-thione and 5-methoxy-3-methylpyrazine-2-carboxylic acid (Prepared as described in Yoshizawa, Kazuhiro et al. PCT Int. Appl., 2013162065)

LC-MS (m/z) 440.1 (MH+) $t_R$=0.58 minutes (Method A) $^1$H NMR (600 MHz, DMSO-d$_6$) δ 10.42 (s, 1H), 8.23 (s, J=0.5 Hz, 1H), 7.88-7.83 (m, 1H), 7.76 (dd, J=7.1, 2.7 Hz, 1H), 7.12 (dd, J=11.9, 8.8 Hz, 1H), 6.23 (s, 2H), 3.99 (s, 3H), 2.75 (s, 3H), 2.73-2.58 (m, 1H), 2.49-2.38 (m, 1H), 1.67 (d, J=22.7 Hz, 3H), 1.63 (s, 3H)

Example 20

N-(3-((2R,5S)-6-amino-3,3,5-trifluoro-2,5-dimethyl-2,3,4,5-tetrahydropyridin-2-yl)-4-fluorophenyl)-5-methyl-1,3,4-oxadiazole-2-carboxamide

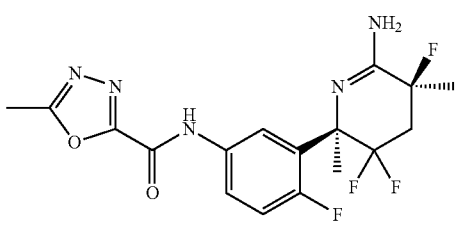

Prepared from (3S,6R)-6-(5-amino-2-fluorophenyl)-3,5,5-trifluoro-3,6-dimethylpiperidine-2-thione and 5-methyl-1,3,4-oxadiazole-2-carboxylic acid LC-MS (m/z) 400.1 (MH$^+$) $t_R$=0.42 minutes (Method A) $^1$H NMR (600 MHz, DMSO-d$_6$) δ 11.51 (d, J=37.6 Hz, 1H), 11.40 (s, 1H), 10.01 (s, 1H), 9.89 (s, 1H), 8.06-8.01 (m, 1H), 7.97 (dd, J=7.3, 2.5 Hz, 1H), 7.35 (dd, J=12.3, 9.0 Hz, 1H), 3.18-3.04 (m, 1H), 2.93-2.80 (m, 1H), 2.64 (s, 3H), 1.94-1.89 (m, 6H)

Example 21

N-(3-((2R,5S)-6-amino-3,3,5-trifluoro-2,5-dimethyl-2,3,4,5-tetrahydropyridin-2-yl)-4-fluorophenyl)-3-methyl-1,2,4-oxadiazole-5-carboxamide

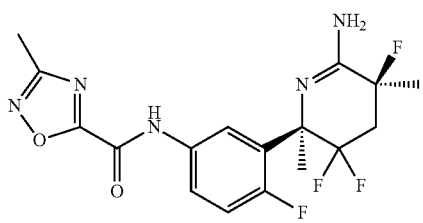 [SMILES: Cc1noc(C(=O)Nc2ccc(F)c([C@@]3(C)N=C(N)[C@@](C)(F)CC3(F)F)c2)n1]

Prepared from (3S,6R)-6-(5-amino-2-fluorophenyl)-3,5,5-trifluoro-3,6-dimethylpiperidine-2-thione and 3-methyl-1,2,4-oxadiazole-5-carboxylic acid LC-MS (m/z) 400 (MH$^+$) $t_R$=0.46 minutes (Method A) $^1$H NMR (600 MHz, DMSO-d$_6$) δ 11.54 (s, 1H), 11.40 (s, 1H), 10.01 (s, 1H), 9.89 (s, 1H), 8.06-8.00 (m, 1H), 7.97 (dd, J=7.3, 2.5 Hz, 1H), 7.34 (dd, J=12.3, 9.0 Hz, 1H), 3.19-3.04 (m, 1H), 2.92-2.79 (m, 1H), 2.64 (s, 3H), 1.92 (m, 6H)

Example 22

N-(3-((2R,5S)-6-amino-3,3,5-trifluoro-2,5-dimethyl-2,3,4,5-tetrahydropyridin-2-yl)-4-fluorophenyl)-1-methyl-1H-1,2,4-triazole-3-carboxamide

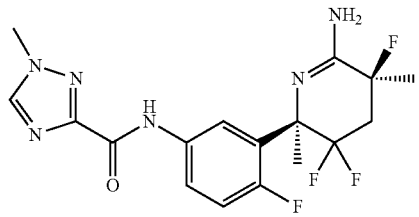 [SMILES: Cn1cnc(C(=O)Nc2ccc(F)c([C@@]3(C)N=C(N)[C@@](C)(F)CC3(F)F)c2)n1]

Prepared from (3S,6R)-6-(5-amino-2-fluorophenyl)-3,5,5-trifluoro-3,6-dimethylpiperidine-2-thione and 1-methyl-1H-1,2,4-triazole-3-carboxylic acid LC-MS (m/z) 399 (MH$^+$) $t_R$=0.39 minutes (Method A) $^1$H NMR (600 MHz, DMSO-d$_6$) δ 10.40 (s, 1H), 8.68 (s, 1H), 7.84 (dd, J=7.2, 2.7 Hz, 1H), 7.82-7.76 (m, 1H), 7.12 (dd, J=11.9, 8.8 Hz, 1H), 6.50-6.03 (s, 2H), 3.98 (s, 3H), 2.75-2.60 (m, 1H), 2.49-2.35 (m, 1H), 1.68 (d, J=22.8 Hz, 3H), 1.62 (s, 3H)

Example 23

N-(3-((2R,5R)-6-amino-3,3,5-trifluoro-2,5-dimethyl-2,3,4,5-tetrahydropyridin-2-yl)-4-fluorophenyl)-1-(difluoromethyl)-1H-pyrazole-3-carboxamide

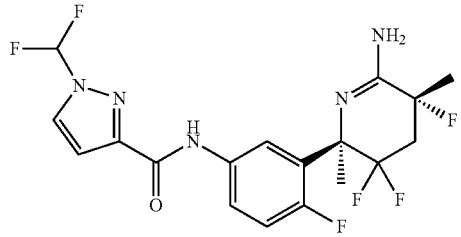 [SMILES: C[C@@]1(F)CC(F)(F)[C@@](C)(c2cc(NC(=O)c3ccn(C(F)F)n3)ccc2F)N=C1N]

Prepared from (3R,6R)-6-(5-amino-2-fluorophenyl)-3,5,5-trifluoro-3,6-dimethylpiperidine-2-thione and 1-(difluoromethyl)-1H-pyrazole-3-carboxylic acid LC-MS (m/z) 434 (MH$^+$) $t_R$=0.5 minutes (Method A) $^1$H NMR (600 MHz, DMSO-d$_6$) δ 10.49 (s, 1H), 8.41 (t, J=3.4 Hz, 1H), 7.92 (t, J=58.7 Hz, 1H), 7.80-7.64 (m, 2H), 7.13 (dd, J=11.9, 8.7 Hz, 1H), 7.01 (d, J=2.7 Hz, 1H), 6.32 (s, 2H), 2.63-2.45 (d, J=23.4 Hz, 1H), 2.28-2.11 (m, 1H), 1.69 (d, J=23.3 Hz, 3H), 1.67 (s, 3H)

Example 24

N-(3-((2R,5R)-6-amino-3,3,5-trifluoro-2,5-dimethyl-2,3,4,5-tetrahydropyridin-2-yl)-4-fluorophenyl)-5-(difluoromethyl)pyrazine-2-carboxamide

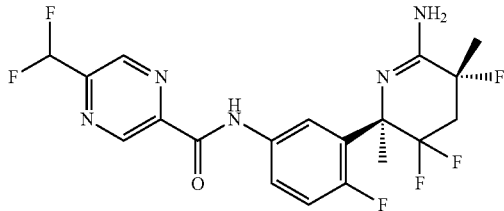 [SMILES: C[C@@]1(F)CC(F)(F)[C@@](C)(c2cc(NC(=O)c3cnc(C(F)F)cn3)ccc2F)N=C1N]

Prepared from (3R,6R)-6-(5-amino-2-fluorophenyl)-3,5,5-trifluoro-3,6-dimethylpiperidine-2-thione and 5-(difluoromethyl)pyrazine-2-carboxylic acid LC-MS (m/z) 446 (MH$^+$) t$_R$=0.52 minutes (Method A) $^1$H NMR (600 MHz, DMSO-d$_6$) δ 11.03 (s, 1H), 9.37 (t, J=2.4 Hz, 1H), 9.09 (s, 1H), 7.89-7.80 (m, 2H), 7.26 (t, J=53.9 Hz, 1H), 7.18 (dd, J=11.9, 8.7 Hz, 1H), 6.34 (s, 2H), 2.62-2.51 (m, 1H), 2.29-2.14 (m, 1H), 1.71 (d, J=23.2 Hz, 3H), 1.68 (s, 3H)

Example 25

N-(3-((2R,5R)-6-amino-3,3,5-trifluoro-2,5-dimethyl-2,3,4,5-tetrahydropyridin-2-yl)-4-fluorophenyl)-5-methoxypyrazine-2-carboxamide

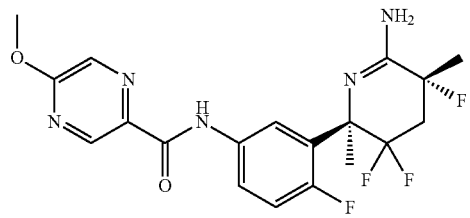 [SMILES: COc1cnc(C(=O)Nc2ccc(F)c([C@@]3(C)N=C(N)[C@](C)(F)CC3(F)F)c2)cn1]

Prepared from (3R,6R)-6-(5-amino-2-fluorophenyl)-3,5,5-trifluoro-3,6-dimethylpiperidine-2-thione and 5-methoxypyrazine-2-carboxylic acid LC-MS (m/z) 426 (MH$^+$) t$_R$=0.5 minutes (Method A) $^1$H NMR (600 MHz, DMSO-d$_6$) δ 10.63 (s, 1H), 8.88 (d, J=1.3 Hz, 1H), 8.41 (d, J=1.3 Hz, 1H), 7.82 (dd, J=7.2, 2.6 Hz, 1H), 7.78 (dt, J=8.6, 3.4 Hz, 1H), 7.14 (dd, J=11.9, 8.8 Hz, 1H), 6.31 (s, 2H), 4.02 (s, 3H), 2.60-2.49 (m, 1H), 2.28-2.13 (m, 1H), 1.70 (d, J=23.0 Hz, 3H), 1.67 (s, 3H)

Example 26

N-(3-((2R,5R)-6-amino-3,3,5-trifluoro-2,5-dimethyl-2,3,4,5-tetrahydropyridin-2-yl)-4-fluorophenyl)-5-methoxypyrimidine-2-carboxamide

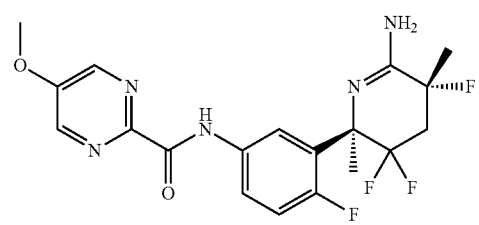 [SMILES: COc1cnc(C(=O)Nc2ccc(F)c([C@@]3(C)N=C(N)[C@](C)(F)CC3(F)F)c2)nc1]

Prepared from (3R,6R)-6-(5-amino-2-fluorophenyl)-3,5,5-trifluoro-3,6-dimethylpiperidine-2-thione and 5-methoxypyrimidine-2-carboxylic acid LC-MS (m/z) 426 (MH$^+$) t$_R$=0.45 minutes (Method A) $^1$H NMR (600 MHz, DMSO-d$_6$) δ 11.65 (s, 1H), 10.99 (s, 1H), 10.20 (s, 1H), 10.08 (s, 1H), 8.74 (s, 2H), 8.13 (m, 1H), 8.05 (d, J=7.1 Hz, 1H), 7.34 (t, J=10.6 Hz, 1H), 4.04 (s, 3H), 3.13-2.99 (m, 1H), 2.76-2.60 (m, 1H), 1.97-1.86 (m, 6H)

Example 27

N-(3-((2R,5R)-6-amino-3,3,5-trifluoro-2,5-dimethyl-2,3,4,5-tetrahydropyridin-2-yl)-4-fluorophenyl)-4-methylthiazole-2-carboxamide

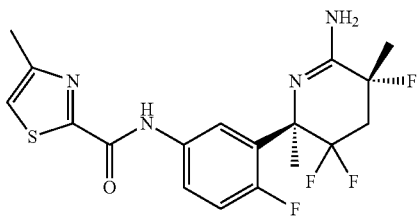 [SMILES: Cc1csc(C(=O)Nc2ccc(F)c([C@@]3(C)N=C(N)[C@](C)(F)CC3(F)F)c2)n1]

Prepared from (3R,6R)-6-(5-amino-2-fluorophenyl)-3,5,5-trifluoro-3,6-dimethylpiperidine-2-thione and 4-methylthiazole-2-carboxylic acid LC-MS (m/z) 415 (MH$^+$) t$_R$=0.54 minutes (Method A) $^1$H NMR (600 MHz, DMSO-d$_6$) δ 10.89 (s, 1H), 7.83-7.76 (m, 2H), 7.69 (d, J=0.9 Hz, 1H), 7.15 (dd, J=11.9, 8.8 Hz, 1H), 6.40 (s, 2H), 2.59-2.52 (m, 1H), 2.50 (s, 3H), 2.19 (m, 1H), 1.74-1.67 (m, 6H)

Example 28

N-(3-((2R,5R)-6-amino-3,3,5-trifluoro-2,5-dimethyl-2,3,4,5-tetrahydropyridin-2-yl)-4-fluorophenyl)-5-(trifluoromethyl)picolinamide

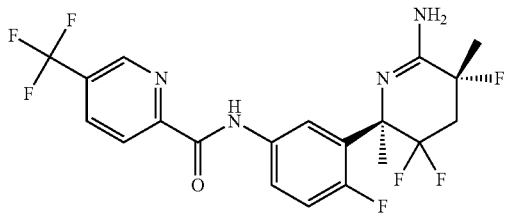 [SMILES: C[C@@]1(F)CC(F)(F)[C@@](C)(c2cc(NC(=O)c3ccc(C(F)(F)F)cn3)ccc2F)N=C1N]

Prepared from (3R,6R)-6-(5-amino-2-fluorophenyl)-3,5,5-trifluoro-3,6-dimethylpiperidine-2-thione and 5-(trifluoromethyl)picolinic acid LC-MS (m/z) 463 (MH$^+$) t$_R$=0.61 minutes (Method A) $^1$H NMR (600 MHz, DMSO-d$_6$) δ 10.96 (s, 1H), 9.18-9.09 (m, 1H), 8.48 (dd, J=8.3, 2.1 Hz, 1H), 8.33 (d, J=8.2 Hz, 1H), 7.89-7.81 (m, 2H), 7.17 (dd, J=11.9, 8.7 Hz, 1H), 6.58-6.29 (m, 2H), 2.62-2.52 (m, 1H), 2.31-2.16 (m, 1H), 1.77-1.66 (m, 6H)

Example 29

N-(3-((2R,5R)-6-amino-3,3,5-trifluoro-2,5-dimethyl-2,3,4,5-tetrahydropyridin-2-yl)-4-fluorophenyl)-2-(difluoromethyl)oxazole-4-carboxamide

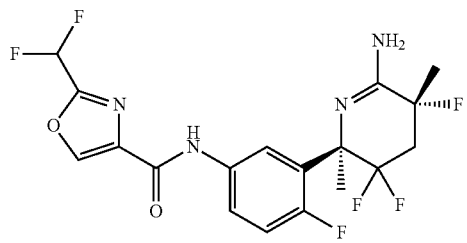 [SMILES: C[C@@]1(F)CC(F)(F)[C@@](C)(c2cc(NC(=O)c3coc(C(F)F)n3)ccc2F)N=C1N]

Prepared from (3R,6R)-6-(5-amino-2-fluorophenyl)-3,5,5-trifluoro-3,6-dimethylpiperidine-2-thione and 2-(difluoromethyl)oxazole-4-carboxylic acid LC-MS (m/z) 435 (MH$^+$) t$_R$=0.51 minutes (Method A) $^1$H NMR (600 MHz, DMSO-d$_6$) δ 10.52 (s, 1H), 9.03 (s, 1H), 7.73 (dd, J=7.2, 2.6 Hz, 1H), 7.72-7.68 (m, 1H), 7.33 (t, J=51.9 Hz, 1H), 7.14 (dd, J=11.9, 8.8 Hz, 1H), 6.31 (s, 2H), 2.58-2.48 (m, 1H), 2.25-2.11 (m, 1H), 1.72-1.64 (m, 6H)

Example 30

N-(3-((2R,5R)-6-amino-3,3,5-trifluoro-2,5-dimethyl-2,3,4,5-tetrahydropyridin-2-yl)-4-fluorophenyl)-4-(fluoromethyl)oxazole-2-carboxamide

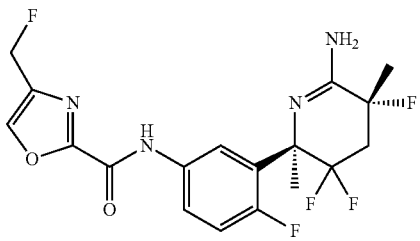 [SMILES: C[C@@]1(F)CC(F)(F)[C@@](C)(c2cc(NC(=O)c3nc(CF)co3)ccc2F)N=C1N]

Prepared from (3R,6R)-6-(5-amino-2-fluorophenyl)-3,5,5-trifluoro-3,6-dimethylpiperidine-2-thione and 4-(fluoromethyl)oxazole-2-carboxylic acid LC-MS (m/z) 417 (MH$^+$) t$_R$=0.47 minutes (Method A) $^1$H NMR (600 MHz, DMSO-d$_6$) δ 11.15 (s, 1H), 8.57 (d, J=5.0 Hz, 1H), 7.81-7.71 (m, 2H), 7.16 (dd, J=11.9, 8.7 Hz, 1H), 6.34 (s, 2H), 5.43 (d, J=48.0 Hz, 2H), 2.58-2.48 (m, 1H), 2.23-2.09 (m, 1H), 1.73-1.64 (m, 6H)

Example 31

N-(3-((2R,5R)-6-amino-3,3,5-trifluoro-2,5-dimethyl-2,3,4,5-tetrahydropyridin-2-yl)-4-fluorophenyl)-4-(fluoromethyl)thiazole-2-carboxamide

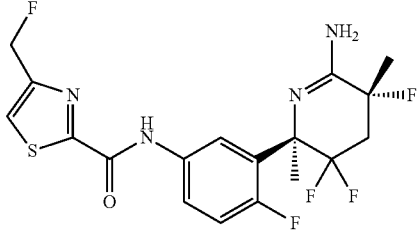 [SMILES: C[C@@]1(F)CC(F)(F)[C@@](C)(c2cc(NC(=O)c3nc(CF)cs3)ccc2F)N=C1N]

Prepared from (3R,6R)-6-(5-amino-2-fluorophenyl)-3,5,5-trifluoro-3,6-dimethylpiperidine-2-thione and 4-(fluoromethyl)thiazole-2-carboxylic acid LC-MS (m/z) 433 (MH$^+$) t$_R$=0.52 minutes (Method A) $^1$H NMR (600 MHz, DMSO-d$_6$) δ 11.03 (s, 1H), 8.25 (d, J=3.2 Hz, 1H), 7.85-7.75 (m, 2H), 7.16 (dd, J=11.9, 8.7 Hz, 1H), 6.35 (dd, J=22.8, 15.9 Hz, 1H), 5.58 (d, J=47.7 Hz, 2H), 2.61-2.52 (m, 1H), 2.19 (m, 1H), 1.76-1.64 (m, 6H)

Example 32

N-(3-((2R,5R)-6-amino-3,3,5-trifluoro-2,5-dimethyl-2,3,4,5-tetrahydropyridin-2-yl)-4-fluorophenyl)-5-cyanopicolinamide

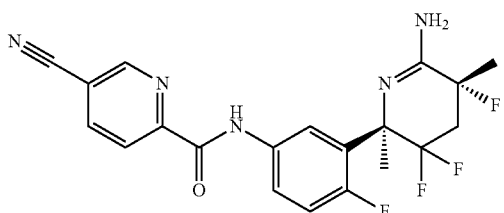

Prepared from (3R,6R)-6-(5-amino-2-fluorophenyl)-3,5,5-trifluoro-3,6-dimethylpiperidine-2-thione and 5-cyanopicolinic acid LC-MS (m/z) 420 (MH$^+$) $t_R$=0.52 minutes (Method A) $^1$H NMR (600 MHz, DMSO-d$_6$) δ 10.96 (s, 1H), 9.20 (dd, J=2.0, 0.8 Hz, 1H), 8.57 (dd, J=8.2, 2.1 Hz, 1H), 8.31-8.26 (m, 1H), 7.87-7.78 (m, 2H), 7.16 (dd, J=11.9, 8.7 Hz, 1H), 6.34 (s, 2H), 2.62-2.52 (m, 1H), 2.28-2.13 (m, 1H), 1.73-1.65 (m, 6H)

Example 33

N-(3-((2R,5R)-6-amino-3,3,5-trifluoro-2,5-dimethyl-2,3,4,5-tetrahydropyridin-2-yl)-4-fluorophenyl)-5-chloropicolinamide

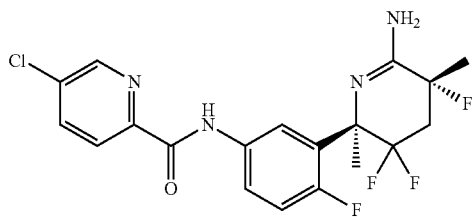 [SMILES: C[C@@]1(F)CC(F)(F)[C@@](C)(c2cc(NC(=O)c3ccc(Cl)cn3)ccc2F)N=C1N]

Prepared from (3R,6R)-6-(5-amino-2-fluorophenyl)-3,5,5-trifluoro-3,6-dimethylpiperidine-2-thione and 5-chloropicolinic acid LC-MS (m/z) 429 (MH$^+$) $t_R$=0.55 minutes (Method A) $^1$H NMR (600 MHz, DMSO-d$_6$) δ 10.80 (s, 1H), 8.80-8.76 (m, 1H), 8.18 (dd, J=8.4, 2.4 Hz, 1H), 8.15 (d, J=8.4 Hz, 1H), 7.85-7.77 (m, 2H), 7.15 (dd, J=11.9, 8.7 Hz, 1H), 6.31 (d, J=25.7 Hz, 2H), 2.58-252 (m, 1H), 2.28-2.15 (m, 1H), 1.75-1.66 (m, 6H)

Example 34

N-(3-((2R,5R)-6-amino-3,3,5-trifluoro-2,5-dimethyl-2,3,4,5-tetrahydropyridin-2-yl)-4-fluorophenyl)-2-methyloxazole-4-carboxamide

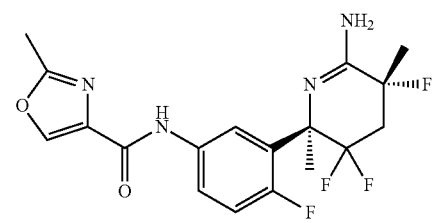 [SMILES: Cc1nc(C(=O)Nc2ccc(F)c([C@@]3(C)N=C(N)[C@](C)(F)CC3(F)F)c2)co1]

Prepared from (3R,6R)-6-(5-amino-2-fluorophenyl)-3,5,5-trifluoro-3,6-dimethylpiperidine-2-thione and 2-methyloxazole-4-carboxylic acid LC-MS (m/z) 399 (MH$^+$) $t_R$=0.46 minutes (Method A) $^1$H NMR (600 MHz, DMSO-d$_6$) δ 10.29 (br s, 1H), 7.79 (m, 1H), 7.72 (m, 1H), 7.59 (s, 1H), 7.13 (dd, J=11.7, 9.0 Hz, 1H), 6.40 (br s, 2H), 2.55 (m, 1H), 2.44 (s, 3H), 2.20 (m, 1H), 1.71 (d, J=23.4 Hz, 3H), 1.69 (s, 3H)

Example 35

N-(3-((2R,5R)-6-amino-3,3,5-trifluoro-2,5-dimethyl-2,3,4,5-tetrahydropyridin-2-yl)-4-fluorophenyl)-5-methyl-1,2,4-oxadiazole-3-carboxamide

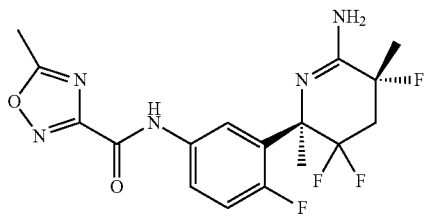 [SMILES: Cc1nc(C(=O)Nc2ccc(F)c([C@@]3(C)N=C(N)[C@](C)(F)CC3(F)F)c2)no1]

Prepared from (3R,6R)-6-(5-amino-2-fluorophenyl)-3,5,5-trifluoro-3,6-dimethylpiperidine-2-thione and 5-methyl-1,2,4-oxadiazole-3-carboxylic acid LC-MS (m/z) 400 (MH$^+$) $t_R$=0.43 minutes (Method A)

Example 36

N-(3-((2R,5R)-6-amino-3,3,5-trifluoro-2,5-dimethyl-2,3,4,5-tetrahydropyridin-2-yl)-4-fluorophenyl)thiazole-2-carboxamide

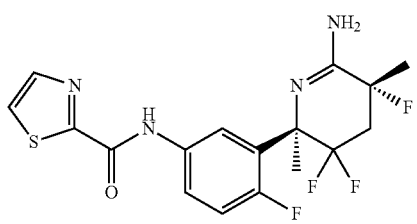 [SMILES: C[C@@]1(F)CC(F)(F)[C@@](C)(c2cc(NC(=O)c3nccs3)ccc2F)N=C1N]

Prepared from (3R,6R)-6-(5-amino-2-fluorophenyl)-3,5,5-trifluoro-3,6-dimethylpiperidine-2-thione and thiazole-2-carboxylic acid LC-MS (m/z) 401 (MH$^+$) t$_R$=0.47 minutes (Method A) $^1$H NMR (600 MHz, DMSO-d$_6$) δ 10.97 (br s, 1H), 8.14 (d, J=3.1 Hz, 1H), 8.10 (d, J=3.1 Hz, 1H), 7.79 (m, 2H), 7.15 (dd, J=11.9, 8.8 Hz, 1H), 6.33 (br s, 2H), 2.55 (m, 1H), 2.18 (m, 1H), 1.70 (d, J=23.0 Hz, 3H), 1.67 (s, 3H)

Example 37

N-(3-((2R,5R)-6-amino-3,3,5-trifluoro-2,5-dimethyl-2,3,4,5-tetrahydropyridin-2-yl)-4-fluorophenyl)-4-bromo-1-methyl-1H-imidazole-2-carboxamide

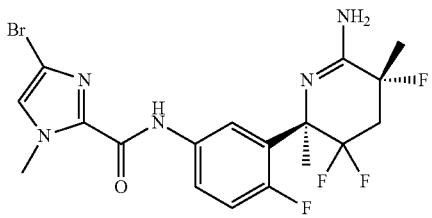 [SMILES: Cn1cc(Br)nc1C(=O)Nc1ccc(F)c([C@@]2(C)N=C(N)[C@](C)(F)CC2(F)F)c1]

Prepared from (3R,6R)-6-(5-amino-2-fluorophenyl)-3,5,5-trifluoro-3,6-dimethylpiperidine-2-thione and 4-bromo-1-methyl-1H-imidazole-2-carboxylic acid LC-MS (m/z) 476 (MH$^+$) t$_R$=0.53 minutes (Method A) $^1$H NMR (600 MHz, DMSO-d$_6$) δ 10.59 (br s, 1H), 7.74 (dt, J=8.7, 3.3 Hz, 1H), 7.69 (dd, J=7.2, 2.6 Hz, 1H), 7.63 (s, 1H), 7.11 (dd, J=11.9, 8.8 Hz, 1H), 6.32 (br s, 2H), 3.95 (s, 3H), 2.55 (m, 1H), 2.18 (m, 1H), 1.69 (d, J=23.1 Hz, 3H), 1.66 (s, 3H)

Example 38

N-(3-((2R,5R)-6-amino-3,3,5-trifluoro-2,5-dimethyl-2,3,4,5-tetrahydropyridin-2-yl)-4-fluorophenyl)-1,4-dimethyl-1H-imidazole-2-carboxamide

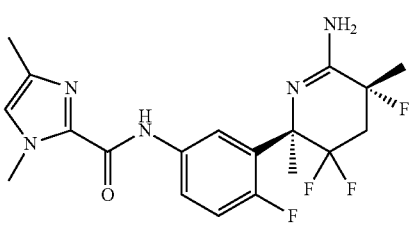 [SMILES: Cc1cn(C)c(C(=O)Nc2ccc(F)c([C@@]3(C)N=C(N)[C@](C)(F)CC3(F)F)c2)n1]

Prepared from (3R,6R)-6-(5-amino-2-fluorophenyl)-3,5,5-trifluoro-3,6-dimethylpiperidine-2-thione and 1,4-dimethyl-1H-imidazole-2-carboxylic acid LC-MS (m/z) 412.3 (MH$^+$) t$_R$=0.46 minutes (Method B) $^1$H NMR (600 MHz, DMSO-d$_6$) δ 10.39 (s, 1H), 7.74-7.71 (m, 1H), 7.68 (dd, J=7.2, 2.6 Hz, 1H), 7.14 (s, J=15.0 Hz, 1H), 7.12-7.07 (m, 1H), 6.30 (s, 2H), 3.91 (s, 3H), 2.58-2.52 (m, 1H), 2.26-2.15 (m, 1H), 2.17 (s, 3H), 1.69 (d, J=23.0 Hz, 3H), 1.66 (s, 3H).

Example 39

N-(3-((2R,5R)-6-amino-3,3,5-trifluoro-2,5-dimethyl-2,3,4,5-tetrahydropyridin-2-yl)-4-fluorophenyl)-1-methyl-1H-pyrazole-3-carboxamide

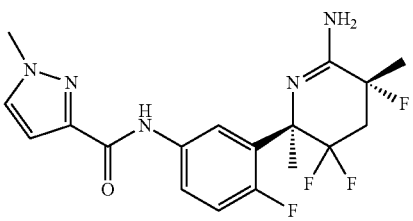 [SMILES: Cn1ccc(C(=O)Nc2ccc(F)c([C@@]3(C)N=C(N)[C@](C)(F)CC3(F)F)c2)n1]

Prepared from (3R,6R)-6-(5-amino-2-fluorophenyl)-3,5,5-trifluoro-3,6-dimethylpiperidine-2-thione and 1-methyl-1H-pyrazole-3-carboxylic acid LC-MS (m/z) 398 (MH$^+$) t$_R$=0.42 minutes (Method B) $^1$H NMR (600 MHz, DMSO-d$_6$) δ 9.93 (br s, 1H), 8.31 (s, 1H), 8.00 (t, J=2.3 Hz, 1H), 7.63 (m, 1H), 7.61 (m, 3H), 6.31 (br s, 2H), 2.56 (m, 1H), 2.21 (m, 1H), 1.69 (d, J=23.3 Hz, 3H), 1.67 (s, 3H)

Example 40

N-(3-((2R,5R)-6-amino-3,3,5-trifluoro-2,5-dimethyl-2,3,4,5-tetrahydropyridin-2-yl)-4-fluorophenyl)-3-methylisoxazole-5-carboxamide

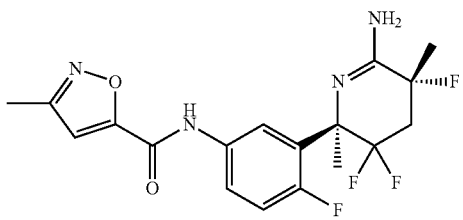 [SMILES: Cc1cc(C(=O)Nc2ccc(F)c([C@@]3(C)N=C(N)[C@](C)(F)CC3(F)F)c2)on1]

Prepared from (3R,6R)-6-(5-amino-2-fluorophenyl)-3,5,5-trifluoro-3,6-dimethylpiperidine-2-thione and 3-methylisoxazole-5-carboxylic acid LC-MS (m/z) 399.1 (MH$^+$) t$_R$=0.47 minutes (Method A) $^1$H NMR (600 MHz, DMSO-d$_6$) δ 10.84 (br s, 1H), 7.73 (m, 1H), 7.70 (dd, J=7.1, 2.7 Hz, 1H), 7.16 (dd, J=11.9, 8.8 Hz, 1H), 7.11 (s, 1H), 6.35 (br s, 2H), 2.55 (m, 1H), 2.34 (s, 3H), 2.20 (m, 1H), 1.68 (d, J=22.6 Hz, 3H), 1.67 (s, 3H)

Example 41

N-(3-((2R,5R)-6-amino-3,3,5-trifluoro-2,5-dimethyl-2,3,4,5-tetrahydropyridin-2-yl)-4-fluorophenyl)-5-methylfuran-2-carboxamide

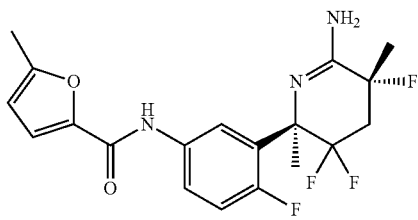 [SMILES: Cc1ccc(C(=O)Nc2ccc(F)c([C@@]3(C)N=C(N)[C@](C)(F)CC3(F)F)c2)o1]

Prepared from (3R,6R)-6-(5-amino-2-fluorophenyl)-3,5,5-trifluoro-3,6-dimethylpiperidine-2-thione and 5-methylfuran-2-carboxylic acid LC-MS (m/z) 398.3 (MH$^+$) t$_R$=0.52 minutes (Method B) $^1$H NMR (600 MHz, DMSO-d$_6$) δ 10.16 (br s, 1H), 7.67 (dd, J=7.2, 2.7 Hz, 1H), 7.63 (ddd, J=8.7, 3.8, 2.9 Hz, 1H), 7.23 (m, 1H), 7.12 (dd, J=11.9, 8.8 Hz, 1H), 6.32 (dd, J=3.4, 1.0 Hz, 1H), 6.31 (br s, 2H), 2.55 (m, 1H), 2.38 (s, 3H), 2.19 (m, 1H), 1.69 (d, J=23.1 Hz, 3H), 1.66 (s, 3H)

Example 42

N-(3-((2R,5R)-6-amino-3,3,5-trifluoro-2,5-dimethyl-2,3,4,5-tetrahydropyridin-2-yl)-4-fluorophenyl)-2-methyloxazole-5-carboxamide trifluoroacetic acid salt

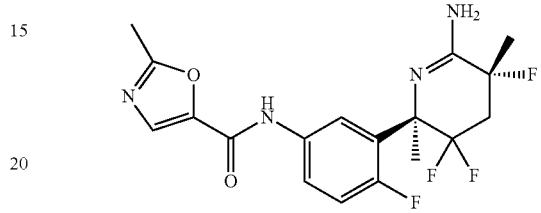

Prepared from (3R,6R)-6-(5-amino-2-fluorophenyl)-3,5,5-trifluoro-3,6-dimethylpiperidine-2-thione and 2-methyloxazole-5-carboxylic acid LC-MS (m/z) 399 (MH$^+$) t$_R$=0.43 minutes (Method A) $^1$H NMR (600 MHz, DMSO-d$_6$) δ 11.64 (s, 1H), 10.62 (s, 1H), 10.17 (s, 1H), 10.07 (s, 1H), 7.90-7.85 (m, 3H), 7.36-7.31 (m, 1H), 3.14-3.02 (m, 1H), 2.77-2.62 (m, 1H), 2.54 (s, 3H), 1.92 (s, 3H), 1.89 (d, J=23.0 Hz, 4H)

Example 43

N-(3-((2R,5R)-6-amino-3,3,5-trifluoro-2,5-dimethyl-2,3,4,5-tetrahydropyridin-2-yl)-4-fluorophenyl)-5-(methoxy-d$_3$)picolinamide

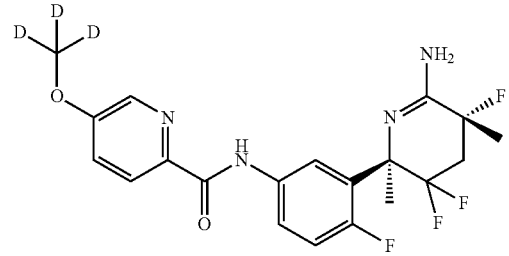 [SMILES: [2H]C([2H])([2H])Oc1ccc(C(=O)Nc2ccc(F)c([C@@]3(C)N=C(N)[C@](C)(F)CC3(F)F)c2)nc1]

Prepared from (3R,6R)-6-(5-amino-2-fluorophenyl)-3,5,5-trifluoro-3,6-dimethylpiperidine-2-thione and 5-(methoxy-d$_3$)picolinic acid LC-MS (m/z) 428.2 (MH$^+$) t$_R$=0.54 minutes (Method A) $^1$H NMR (600 MHz, DMSO-d$_6$) δ 10.58 (s, 1H), 8.39 (d, J=2.9 Hz, 1H), 8.12 (d, J=8.7 Hz, 1H), 7.84-7.81 (m, 1H), 7.78 (d, J=8.1 Hz, 1H), 7.60 (dd, J=8.7, 2.9 Hz, 1H), 7.13 (dd, J=11.8, 8.9 Hz, 1H), 6.32 (s, 2H), 2.59-2.45 (m, 1H), 2.36-2.10 (m, 1H), 1.71 (d, J=23.0 Hz, 3H), 1.67 (s, 3H)

Example 44

N-(3-((2R,5R)-6-amino-3,3,5-trifluoro-2,5-dimethyl-2,3,4,5-tetrahydropyridin-2-yl)-4-fluorophenyl)-4-chlorobenzamide

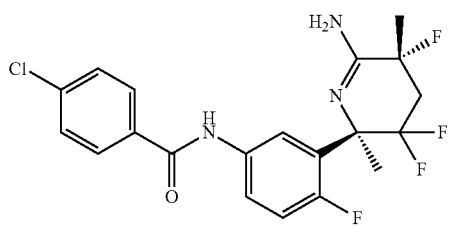 [SMILES: C[C@@]1(F)CC(F)(F)[C@@](C)(c2cc(NC(=O)c3ccc(Cl)cc3)ccc2F)N=C1N]

Prepared from (3R,6R)-6-(5-amino-2-fluorophenyl)-3,5,5-trifluoro-3,6-dimethylpiperidine-2-thione and 4-chlorobenzoic acid LC-MS (m/z) 428.1 (MH$^+$) t$_R$=0.58 minutes (Method A)
$^1$H NMR (600 MHz, DMSO-d$_6$) δ 10.46 (s, 1H), 7.96 (d, J=8.4 Hz, 2H), 7.76-7.65 (m, 2H), 7.60 (d, J=8.4 Hz, 2H), 7.15 (dd, J=11.7, 8.9 Hz, 1H), 6.37 (s, 2H), 2.61-2.49 (m, 1H), 2.29-2.14 (m, 1H), 1.70 (d, J=22.2 Hz, 3H), 1.68 (s, 3H)

Example 45

N-(3-((2R,5S)-6-amino-3,3,5-trifluoro-2,5-dimethyl-2,3,4,5-tetrahydropyridin-2-yl)-4-fluorophenyl)-5-(difluoromethoxy)picolinamide

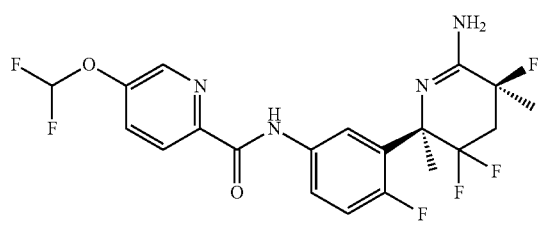 [SMILES: C[C@]1(F)CC(F)(F)[C@@](C)(c2cc(NC(=O)c3ccc(OC(F)F)cn3)ccc2F)N=C1N]

Prepared from (3S,6R)-6-(5-amino-2-fluorophenyl)-3,5,5-trifluoro-3,6-dimethylpiperidine-2-thione and 5-(difluoromethoxy)picolinic acid LC-MS (m/z) 461.1 (MH$^+$) t$_R$=0.55 minutes (Method A)
$^1$H NMR (600 MHz, DMSO-d$_6$) δ 10.59 (s, 1H), 8.62 (d, J=2.8 Hz, 1H), 8.22 (dd, J=8.7, 0.5 Hz, 1H), 7.93-7.89 (m, 2H), 7.89-7.85 (m, 1H), 7.50 (t, J=72.9 Hz, 1H), 7.14 (dd, J=11.9, 8.8 Hz, 1H), 6.23 (s, 2H), 2.74-2.59 (m, 1H), 2.55 (s, 3H), 2.49-2.38 (m, 1H), 1.68 (d, J=22.7 Hz, 3H), 1.63 (s, 3H)

Example 46

N-(3-((2R,5S)-6-amino-3,3,5-trifluoro-2,5-dimethyl-2,3,4,5-tetrahydropyridin-2-yl)-4-fluorophenyl)-3-fluoro-5-methoxypicolinamide

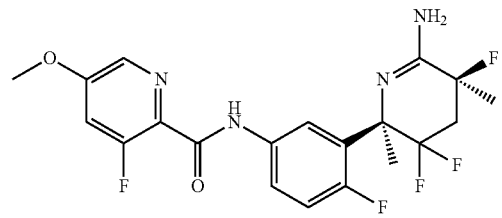

Prepared from (3S,6R)-6-(5-amino-2-fluorophenyl)-3,5,5-trifluoro-3,6-dimethylpiperidine-2-thione and 3-fluoro-5-methoxypicolinic acid LC-MS (m/z) 443.1 (MH$^+$) t$_R$=0.51 minutes (Method A)
$^1$H NMR (600 MHz, DMSO-d$_6$) δ 10.40 (s, 1H), 8.28 (dd, J=2.3, 0.8 Hz, 1H), 7.84-7.81 (m, 1H), 7.78 (dd, J=7.2, 2.7 Hz, 1H), 7.62 (dd, J=12.7, 2.4 Hz, 1H), 7.12 (dd, J=12.0, 8.8 Hz, 1H), 6.22 (s, 2H), 3.94 (s, 3H), 2.72-2.59 (m, 1H), 2.49-2.36 (m, 1H), 1.67 (d, J=22.7 Hz, 3H), 1.62 (s, 3H)

Example 47

N-(3-((2R,5S)-6-amino-3,3,5-trifluoro-2,5-dimethyl-2,3,4,5-tetrahydropyridin-2-yl)-4 fluorophenyl)-2,5-dimethyloxazole-4-carboxamide

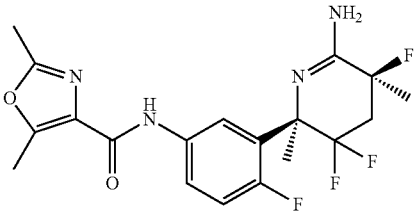 [SMILES: Cc1nc(C(=O)Nc2ccc(F)c([C@@]3(C)N=C(N)[C@@](C)(F)CC3(F)F)c2)c(C)o1]

Prepared from (3S,6R)-6-(5-amino-2-fluorophenyl)-3,5,5-trifluoro-3,6-dimethylpiperidine-2-thione and 2,5-dimethyloxazole-4-carboxylic acid LC-MS (m/z) 413.1 (MH$^+$) t$_R$=0.51 minutes (Method A)
$^1$H NMR (600 MHz, DMSO-d$_6$) δ 9.90 (s, 1H), 7.80 (dd, J=7.2, 2.7 Hz, 1H), 7.75 (ddd, J=8.7, 3.8, 2.9 Hz, 1H), 7.08

(dd, J=12.0, 8.8 Hz, 1H), 6.21 (s, 2H), 2.71-2.60 (m, 1H), 2.57 (s, 3H), 2.47-2.40 (m, 1H), 2.45 (s, 3H), 1.67 (d, J=22.8 Hz, 3H), 1.61 (s, 3H)

Example 48

N-(3-((2R,5S)-6-amino-3,3,5-trifluoro-2,5-dimethyl-2,3,4,5-tetrahydropyridin-2-yl)-5-(methoxy-d3)picolinamide

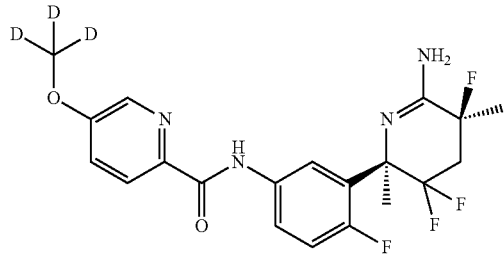 [SMILES: [2H]C([2H])([2H])Oc1ccc(C(=O)Nc2ccc(F)c([C@@]3(C)N=C(N)[C@@](C)(F)CC3(F)F)c2)nc1]

Prepared from (3S,6R)-6-(5-amino-2-fluorophenyl)-3,5,5-trifluoro-3,6-dimethylpiperidine-2-thione and 5-(methoxy-d$_3$)picolinic acid LC-MS (m/z) 428.1 (MH$^+$) t$_R$=0.51 minutes (Method A) $^1$H NMR (600 MHz, DMSO-d$_6$) δ 10.41 (s, 1H), 8.39 (dd, J=2.9, 0.5 Hz, 1H), 8.12 (dd, J=8.7, 0.5 Hz, 1H), 7.88-7.85 (m, 2H), 7.61 (dd, J=8.7, 2.9 Hz, 1H), 7.15-7.09 (m, 1H), 6.22 (s, 2H), 2.72-2.59 (m, 1H), 2.48-2.38 (m, 1H), 1.67 (d, J=22.7 Hz, 3H), 1.62 (s, 3H)

Example 49

N-(3-((2R,5S)-6-amino-3,3,5-trifluoro-2,5-dimethyl-2,3,4,5-tetrahydropyridin-2-yl)-4-fluorophenyl)-5-fluoro-3-methylpicolinamide

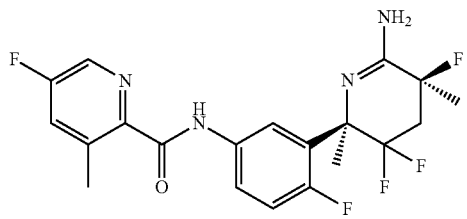 [SMILES: Cc1cc(F)cnc1C(=O)Nc1ccc(F)c([C@@]2(C)N=C(N)[C@@](C)(F)CC2(F)F)c1]

Prepared from (3S,6R)-6-(5-amino-2-fluorophenyl)-3,5,5-trifluoro-3,6-dimethylpiperidine-2-thione and 5-fluoro-3-methylpicolinic acid LC-MS (m/z) 427.1 (MH$^+$) t$_R$=0.54 minutes (Method A) $^1$H NMR (600 MHz, DMSO-d$_6$) δ 10.51 (s, 1H), 8.53 (dd, J=2.7, 0.4 Hz, 1H), 7.89-7.84 (m, 1H), 7.81 (ddd, J=9.8, 2.7, 0.6 Hz, 1H), 7.75 (dd, J=7.2, 2.7 Hz, 1H), 7.12 (dd, J=12.0, 8.8 Hz, 1H), 6.22 (s, 2H), 2.75-2.61 (m, 1H), 2.58 (s, 3H), 2.49-2.37 (m, 1H), 1.67 (d, J=22.7 Hz, 3H), 1.62 (s, 3H)

Example 18a

N-(3-((2R,5S)-6-amino-3,3,5-trifluoro-2,5-dimethyl-2,3,4,5-tetrahydropyridin-2-yl)-4-fluorophenyl)-5-cyano-3-methylpicolinamide

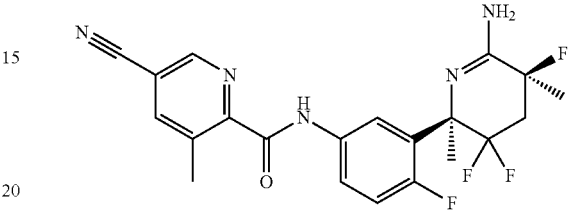

(3S,6R)-6-(5-amino-2-fluorophenyl)-3,5,5-trifluoro-3,6-dimethylpiperidine-2-thione (750 mg, 2.44 mmol) was dissolved in 7M ammonia in methanol (36 ml, 252 mmol). The reaction mixture was stirred in a sealed vial at 60° C. overnight. The reaction mixture was allowed to cool to room temperature and concentrated under reduced pressure to afford (3S,6R)-6-(5-amino-2-fluorophenyl)-3,5,5-trifluoro-3,6-dimethyl-3,4,5,6-tetrahydropyridin-2-amine (708 mg, 2.448 mmol, 100% yield) as a pale yellow solid that was used in the next reaction without further purification.

5-Cyano-3-methylpicolinic acid (232 mg, 1.432 mmol) (Prepared as described in Badiger, Sangamesh et al. PCT Int. Appl., 2012095469) was placed in a round bottom flask and dissolved in DMF (7 mL). HATU (669 mg, 1.760 mmol) was added and the reaction was stirred at room temperature for 5 min, N,N-diisopropylethylamine (0.7 mL, 4.1 mmol) was added. The reaction mixture was cooled to 0° C. and added dropwise to a solution of (3S,6R)-6-(5-amino-2-fluorophenyl)-3,5,5-trifluoro-3,6-dimethyl-3,4,5,6-tetrahydropyridin-2-amine (470 mg, 1.63 mmol) in DMF (7 mL) at 0° C. The reaction mixture was stirred at 0° C. for 30 min then at 30 min at room temperature. The reaction mixture was diluted with ethyl acetate (50 mL) and washed with water. The phases were separated and the aqueous layer was extracted with ethyl acetate (2×100 mL). The combined organic phases were dried over MgSO$_4$, filtered, and concentrated in vacuo. The crude material was purified using a RediSep Automated flash system on 80 g silica gel (eluent: ethyl acetate/heptane). The product was further purified by the following procedure: The product was dissolved in ethyl acetate (50 mL) and washed with a solution of saturated aqueous NaHCO$_3$/water (1/1). The organic phase was washed total of 15 times (using 10 mL each time). The organic phase was dried over MgSO$_4$, filtered, and evaporated to give N-(3-((2R,5S)-6-amino-3,3,5-trifluoro-2,5-dimethyl-2,3,4,5-tetrahydropyridin-2-yl)-4-fluorophenyl)-5-cyano-3-methylpicolinamide (153 mg, 26% yield).

LC-MS (m/z) 434 (MH$^+$) t$_R$=0.53 minutes (Method A).
$^1$H NMR (600 MHz, CDCl$_3$) δ 9.97 (s, 1H), 8.72 (dd, J=1.9, 0.6 Hz, 1H), 7.99-7.90 (m, 2H), 7.44 (dd, J=6.8, 2.8 Hz, 1H), 7.09 (dd, J=11.7, 8.8 Hz, 1H), 4.71 (s, 2H), 2.86 (s, 3H), 2.48 (m, 2H), 1.81-1.74 (m, 6H).

The following compound was prepared in a way similar to example 18a:

Example 4a

N-(3-((2R,5S)-6-amino-3,3,5-trifluoro-2,5-dimethyl-2,3,4,5-tetrahydropyridin-2-yl)-4-fluorophenyl)-5-cyanopicolinamide

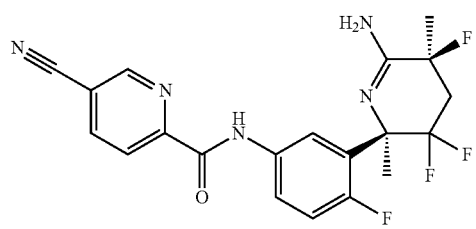 [SMILES: C[C@]1(F)CC(F)(F)[C@@](C)(c2cc(NC(=O)c3ccc(C#N)cn3)ccc2F)N=C1N]

Prepared from (3S,6R)-6-(5-amino-2-fluorophenyl)-3,5,5-trifluoro-3,6-dimethylpiperidine-2-thione and 5-cyanopicolinic acid LC-MS (m/z) 420.0 (MH$^+$) t$_R$=1.79 minutes (Method B)

Stereochemistry

Crystals were obtained by recrystallization of compound 48 from a mixture of heptane and ethyl acetate. The structure of compound 48 was elucidated by X-ray crystallography of said crystals. The two molecules in the asymmetric unit as found in the X-ray structure of compound 48 are shown in FIG. 1 and shows that the stereoconfiguration is (2R,5S).

The absolute configurations of the exemplified compounds of the present invention can thus be rationalized. All examples were synthesized from the intermediates XVIa or XVIb with R$^1$=R$^3$=methyl and R$^7$=tert-butoxy carbonyl intermediate XV (R$^1$=methyl and R$^4$=ethyl) for which the absolute configuration was assigned based on literature precedence (WO2012110459). The two ways of assigning the stereochemistry at the 5-position are in agreement.

The absolute stereochemistry of intermediate XVIb (R$^1$=R$^3$=methyl and R$^7$=tert-butoxy carbonyl) was based on the absolute configuration of intermediate XV (R$^1$=methyl and R$^4$=ethyl) for which the absolute configuration was assigned based on literature precedence. The stereochemistry at the 5-position of the 6-amino-3,3,5-trifluoro-2,5-dimethyl-2,3,4,5-tetrahydropyridine substructure is opposite to the stereochemistry at that position of intermediate XVIa (R$^1$=R$^3$=methyl and R$^7$=tert-butoxy carbonyl), hence, the stereochemistry of intermediate XVIb is (2R,5S).

The stereochemistry of the exemplified compounds containing the (2R,5R)-6-amino-3,3,5-trifluoro-2,5-dimethyl-2,3,4,5-tetrahydropyridine substructure, e.g. example 2, is based on the stereochemistry of intermediate XVIb (R$^1$=R$^3$=methyl and R$^7$=tert-butoxy carbonyl).

Pharmacological Testing

BACE1 Binding Assay

The binding assay was performed as SPA-based assay using a biotinylated form of human BACE1 recombinantly expressed and subsequently purified from Freestyle HEK293 cells. The binding assay was run in a 50 mM sodium acetate buffer, pH 4.5 containing 50 mM NaCl and 0.03% Tween-20 in white clear bottom 384 plates (Corning #3653). 10 nM (final concentration) radioligand ([$^3$H]—N-((1S,2R)-1-benzyl-3-cyclopropylamino-2-hydroxy-propyl)-5-(methanesulfonyl-methyl-amino)-N—((R)-1-phenyl-ethyl)-isophthalamide) (TRQ11569 purchased from GE Healthcare) was mixed with test compound at a given concentration, 6 nM (final concentration) human BACE1 and 25 µg Streptavidin coated PVT core SPA beads (RPNQ0007, GE Healthcare Life Sciences) in a total volume of 40 µl. Several concentra- Scheme 4. Rationale for assignment of absolute and relative stereochemistry of the exemplified compounds.
R$^1$ = R$^3$ = methyl, R$^4$ = ethyl and R$^7$ = tert-butoxy carbonyl

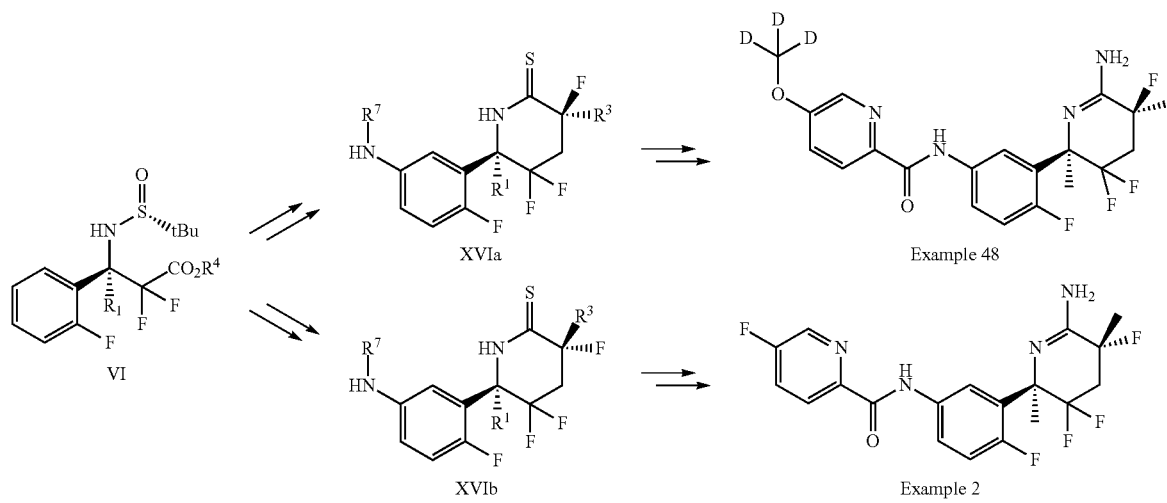

The relative and absolute stereochemistry of intermediate XVIa (R$^1$=R$^3$=methyl and R$^7$=tert-butoxy carbonyl) has been assigned as (2R,5S) based on the X-ray structure of example 48. The absolute stereochemistry of the 2-position in intermediate XVIa (R$^1$=R$^3$=methyl and R$^7$=tert-butoxy carbonyl) was assigned as (2R) based on the absolute configuration of tions of each test compound were tested in the assay for IC$_{50}$ determination. The plates were incubated for one hour at room temperature and counted in a Wallac Trilux counter. Total and non-specific binding were determined using buffer and 1 µM (final concentration) of the high affinity BACE1 reference inhibitor (S)-6-[3-chloro-5-(5-prop-1-ynyl-pyridin-3-yl)-thiophen-2-yl]-2-imino-3,6-dimethyl-tetrahydro-pyrimidin-4-one, respectively. For each test compound, a $IC_{50}$ value (the concentration mediating 50% inhibition of the specific binding of the radioligand) was determined from concentration-response curve and used to calculate the $K_i$ from the equation $K_i=IC_{50}/(1+L/K_d)$, where L and $K_d$ are the final concentration of the radioligand used in the assay and the dissociation constant of the radioligand, respectively. The $K_d$ of the radioligand was determined from saturation binding experiments.

quently read in a Pherastar (Ex540/Em590). The enzyme activity observed in presence of test compound were normalized to the enzyme activity observed in presence of buffer and 10 µM (final concentration) of the high affinity BACE1 reference inhibitor (S)-6-[3-Chloro-5-(5-prop-1-ynyl-pyridin-3-yl)-thiophen-2-yl]-2-imino-3,6-dimethyl-tetra-hydropyrimidin-4-one, respectively. The efficacy of the test compounds was evaluated at 10 µM (final concentration) and defined as the percent inhibition of the enzyme activity using the equation % inhibition=100%−normalized enzyme activity in percent.

TABLE 1 binding affinity of selected compounds

| Compound No | BACE1 Ki (nM) |
|---|---|
| 1 | 83 |
| 2 | 210 |
| 3 | 12 |
| 4 | 11 |
| 5 | 18 |
| 6 | 19 |
| 7 | 33 |
| 8 | 66 |
| 9 | 100 |
| 10 | 44 |
| 11 | 63 |
| 12 | 29 |
| 13 | 28 |
| 14 | 37 |
| 15 | 46 |
| 16 | 58 |
| 17 | 11 |
| 18 | 4.3 |
| 19 | 32 |
| 20 | 1600 |
| 21 | 58 |
| 22 | 110 |
| 23 | 71 |
| 24 | 420 |
| 25 | 130 |
| 26 | 130 |
| 27 | 140 |
| 28 | 170 |
| 29 | 92 |
| 30 | 260 |
| 31 | 92 |
| 32 | 51 |
| 33 | 62 |
| 34 | 210 |
| 35 | 680 |
| 36 | 390 |
| 37 | 420 |
| 38 | 1000 |
| 39 | 4800 |
| 40 | 8200 |
| 41 | 520 |
| 42 | 1500 |
| 43 | 91 |
| 44 | 740 |
| 45 | 14 |
| 46 | 14 |
| 47 | 65 |
| 48 | 14 |
| 49 | 60 |

TABLE 2

BACE1 activity of selected compounds

| Compound No | BACE1 inhibition at 10 µM (%) |
|---|---|
| 1 | 104 |
| 2 | 100 |
| 3 | 102 |
| 4 | 99 |
| 5 | 96 |
| 6 | 100 |
| 7 | 100 |
| 8 | 104 |
| 9 | 103 |
| 10 | 102 |
| 11 | 99 |
| 12 | 104 |
| 13 | 99 |
| 14 | 102 |
| 15 | 101 |
| 16 | 105 |
| 17 | 101 |
| 18 | 102 |
| 19 | 98 |
| 20 | 88 |
| 21 | 102 |
| 22 | 92 |
| 23 | 102 |
| 24 | 98 |
| 25 | 102 |
| 26 | 102 |
| 27 | 98 |
| 28 | 102 |
| 29 | 101 |
| 30 | 103 |
| 31 | 102 |
| 32 | 101 |
| 33 | 103 |
| 34 | 102 |
| 35 | 100 |
| 36 | 100 |
| 37 | 104 |
| 38 | 98 |
| 39 | 74 |
| 40 | 69 |
| 41 | 93 |
| 42 | 84 |
| 43 | 94 |
| 44 | 92 |
| 45 | 103 |
| 46 | 101 |
| 47 | 102 |
| 48 | 99 |
| 49 | 98 |

BACE1 Efficacy Assay

The efficacy assay was performed as a FRET-based assay using a commercially available BACE1 kit (Life Technologies, P2985). 2 µl test compound at 10 µM (final concentration) and 15 µl BACE1 enzyme from the kit (final concentration 3 nM) were preincubated for 15 minutes at room temperature before addition of 15 µl of substrate from the kit (250 nM final concentration) and incubated for additional 90 minutes at room temperature. The assay plate was subse- Assessment of Aβ Levels in Rat Brain and Plasma Following BACE1 Inhibition.

Animals.

All rat care and experimental procedures were approved by Lundbeck Veterinary Staff, according to Danish legislature. The rats were maintained in a barrier facility with a 12/12-h light/dark cycle and ad libitum food and water access.

Treatment of Naïve Rats.

Young adult Male Sprague Dawley rats of approximately 250 g weight were purchased from Charles River and received 0-30 mg/kg of vehicle (10% HP betaCD+1M MeSO$_4$, pH 2.5) or test compounds (dissolved in vehicle) only by oral gavage (p.o). The compounds are dosed at a volume of 5 ml/kg. Cohorts of 5-10 animals were established for each treatment condition.

The animals undergoing treatment were closely monitored by veterinary staff for any signs of toxicity. Monitoring parameters included body weight, physical appearance, changes in coat appearance, occurrence of unprovoked behavior, and blunted or exaggerated responses to external stimuli.

Tissue Collection.

At T=180 minutes after initial dosing the animals were stunned and decapitated with a guillotine. Trunk-blood was sampled in EDTA coated tubes after decapitation of the animal. The blood was centrifuged at 2200 G at 4° C. for 15 minutes and the plasma was collected and frozen at −80° C. The blood was aliquoted for Aβ ELISA and DMPK analysis Immediately following sacrifice, the brain was extracted and split into 2 halves. The right hemibrains were snap frozen on dry ice and stored at −80° C. The left half was dissected; with the front forebrain taken for Aβ ELISA and the remainder used for DMPK analysis. These samples were also snap frozen on dry ice and stored at −80° C. until use for analysis.

Tissue Processing.

The cortex samples were thawed slightly on wet ice before they were homogenized with a small volume dispersing instrument (T10 basic ULTRA-TURRAX®) which was set at speed 5 for approximately 5-7 sec. The tissue was processed in a 10 times volume of the weight, for example 100 mg of tissue was homogenized in 1000 µL of Homogenization buffer. Homogenization buffer: 50 ml Milli Q water+50 nM NaCl+0.2% Diethylamin (DEA)+1 tablet of Complete Protease inhibitor cocktail+1 nM 4-(2-aminoethyl)benzenesulfonyl fluoride hydrochloride irreversible serine protease inhibitor (AEBSF).

After homogenization 450 µL aliquots of the samples are collected into a 1.5 ml Eppendorf tube and placed on wet ice, 0.5% NP-40 (50 ul) was added to all samples and then they were incubated on ice for 30 min. After which all samples were sonicated using an Ultrasonic homogenizer with 20 kHz homogeneous sound (SONOPLUS HD2070, Bandelin Electronic) 10 pulse set at 12-13% power to extract all the Aβ species. The samples were then centrifuged (Ole Dich 157 MPRF Micro centrifuge) at 20000 G for 20 minutes at 4° C. After centrifugation 285 µL of the supernatant was pipetted into 600 µL microtubes tubes and neutralized with 15 µL of 1M Tris-HCL buffer.

ELISA Protocol.

WAKO 294-62501 Human/Rat Abeta amyloid (40) kit was used for all ELISA analyses. 30 µL plasma samples or 30 µL of the cortex supernatants generated as described above were placed in 600 µL microtubes tubes on wet ice. To this 30 µL of 8M Urea (AppliChem A1049, 9025) are added to generate a 2-fold dilution. Both plasma and cortex supernatants are incubated on ice for 30 min. Standard rows were prepared from the standard peptide stock provided in the kit and standard diluent containing 1.6M Urea (200 µL 8M Urea+800 µL of standard diluent) and 0.8M Urea (400 µL 8M Urea+3600 µL Standard diluent). A serial 2-fold dilution of Aβ40 from 100 pmol/ml to 0 pmol/L was prepared for the assay.

After incubation with urea, all samples were further diluted by addition of 5 times standard diluent from the Kit. This was done by adding 240 µL Standard Diluent to 60 µL sample/urea mixture, which was then mixed well. 100 µL of each diluted sample was pipetted into designated wells of the ELISA plate in duplicates. The plate was then covered and incubated overnight at 4° C. The following day, the ELISA kit was brought to room temperature before use. The incubated plate was washed 5 times with the 20× washing solution diluted in Milli Q water. 100 µL HRP-conjugate was applied to each well, and the plate was covered and incubates at 4° C. for 1 hr. The wash was repeated again for 5 times. 100 µL 3,3',5,5'-Tetramethylbenzidine (TMB) solution was applied to each well and the plate was covered and incubated in the dark at room temperature for 30 minutes. 100 µL STOP-solution was next applied to each well, and the plate was read at 450 nm wavelength in a spectrophotometer (Labsystems Multiscan Ascent) within 30 min of adding the STOP-solution to the wells.

Concentration of Aβ in the samples was determined based on a standard curve generated from standards containing known concentrations of synthetic Aβ40. Those skilled in the art will appreciate that diethylamine (DEA) and urea extractions will release soluble Aβ, and insoluble Aβ respectively. Since the ELISA kit is validated and widely used, it is accepted that as long as the treatment conditions and assay conditions are the same for each compound tested, then the assay should yield consistent robust data for the compounds tested and produce minimal discrepancies.

Data Analysis

To determine the concentration of Aβ40 in the samples, the interpolated values of the samples loaded on plates are multiplied by 20 to account for the dilutions made when the volumes of DEA, urea and neutralization solution were added up. Values are calculated as percentage change in Aβ40 compared to vehicle treated animals.

Compounds 1, 5, 17, 18, and 24 were administered at doses of 10 or 30 mg/kg p.o. and brain and plasma samples were collected at 3 hours post dose and the following exposures and reductions in Aβ40 levels were measured as described above.

TABLE 3

Results for compound 1

| | Dose (mg/kg) | Exp (ng/g) | Brain/Plasma ratio | Aβ40 reduction (%) |
|---|---|---|---|---|
| Brain Rat | 30 | 2188 | 0.62 | 56 |
| Plasma Rat | | 3545 | | 41 |

TABLE 4

Results for compound 5

| | Dose (mg/kg) | Exp (ng/g) | Brain/Plasma ratio | Aβ40 reduction (%) |
|---|---|---|---|---|
| Brain Rat | 10 | 174 | 1.3 | 34 |
| Plasma Rat | | 137 | | 34 |
| Brain Rat | 30 | 954 | 1.5 | 61 |
| Plasma Rat | | 632 | | 39 |

TABLE 5

Results for example 17

| | Dose (mg/kg) | Exp (ng/g) | Brain/Plasma ratio | Aβ40 reduction (%) |
|---|---|---|---|---|
| Brain Rat | 30 | 1223 | 1.48 | 63 |
| Plasma Rat | | 828 | | 49 |

TABLE 6

Results for example 18

| | Dose (mg/kg) | Exp (ng/g) | Brain/Plasma ratio | Aβ40 reduction (%) |
|---|---|---|---|---|
| Brain Rat | 10 | 412 | 0.53 | 66 |
| Plasma Rat | | 778 | | 54 |
| Brain Rat | 30 | 1606 | 0.54 | 61 |
| Plasma Rat | | 3000 | | 50 |

TABLE 7

Results for example 24

| | Dose (mg/kg) | Exp (ng/g) | Brain/Plasma ratio | Aβ40 reduction (%) |
|---|---|---|---|---|
| Brain Rat | 10 | 134 | 1.39 | 15 |
| Plasma Rat | | 96.2 | | 28 |
| Brain Rat | 30 | 809 | 1.20 | 49 |
| Plasma Rat | | 673 | | 61 |

As shown in tables 3-7, compounds of the present invention are able to penetrate the blood brain barrier and are efficacious in lowering Aβ40 levels in the brain of animals.

The invention claimed is:

1. A compound of formula I

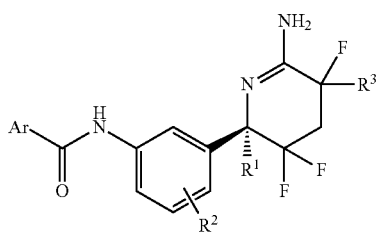

Formula I

Ar is selected from the group consisting of phenyl, pyridyl, pyrimidyl, pyrazinyl, imidazolyl, pyrazolyl, 1,2,4-triazolyl, thiophenyl, thiazolyl, oxazolyl, isoxazolyl, 1,3,4-thiadiazolyl, isothiazolyl, 1,3,4-oxadiazolyl, 1,2,4-oxadiazolyl, furanyl, furazanyl and 1,2,4-thiadiazolyl and where the Ar is optionally substituted with one or more halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy;

$R^1$ is $C_1$-$C_3$ alkyl or $C_1$-$C_3$ fluoroalkyl;

$R^2$ is hydrogen, halogen, $C_1$-$C_3$ fluoroalkyl or $C_1$-$C_3$ alkyl; and $R^3$ is $C_1$-$C_3$ alkyl; or a pharmaceutically acceptable salt thereof.

2. A compound according to claim 1, wherein the compound is of formula Ia

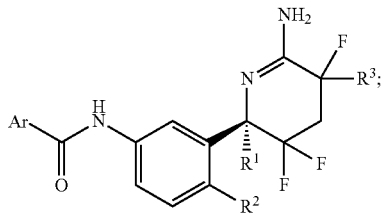

Formula Ia or a pharmaceutically acceptable salt thereof.

3. The compound of claim 1, wherein $R^1$ is $CH_3$.

4. The compound of claim 1, wherein $R^2$ is F or H.

5. The compound of claim 1, wherein $R^3$ is $CH_3$.

6. The compound of claim 1, wherein Ar is optionally substituted with one or more F, Cl, CN, $C_1$-$C_3$ alkyl, $C_1$-$C_3$ fluoroalkyl or $C_1$-$C_3$ alkoxy.

7. The compound of claim 1, wherein the stereochemistry is (2R,5S).

8. The compound of claim 1, wherein the compound is selected from the group consisting of:
  (1) N-(3-((2R,5S)-6-amino-3,3,5-trifluoro-2,5-dimethyl-2,3,4,5-tetrahydropyridin-2-yl)-4-fluorophenyl)-5-fluoropicolinamide;
  (2) N-(3-((2R,5R)-6-amino-3,3,5-trifluoro-2,5-dimethyl-2,3,4,5-tetrahydropyridin-2-yl)-4-fluorophenyl)-5-fluoropicolinamide;
  (3) N-(3-((2R,5S)-6-amino-3,3,5-trifluoro-2,5-dimethyl-2,3,4,5-tetrahydropyridin-2-yl)-4-fluorophenyl)-5-chloropicolinamide;
  (4) N-(3-((2R,5S)-6-amino-3,3,5-trifluoro-2,5-dimethyl-2,3,4,5-tetrahydropyridin-2-yl)-4-fluorophenyl)-5-cyanopicolinamide;
  (5) N-(3-((2R,5S)-6-amino-3,3,5-trifluoro-2,5-dimethyl-2,3,4,5-tetrahydropyridin-2-yl)-4-fluorophenyl)-5-methoxypyrazine-2-carboxamide;
  (6) N-(3-((2R,5S)-6-amino-3,3,5-trifluoro-2,5-dimethyl-2,3,4,5-tetrahydropyridin-2-yl)-4-fluorophenyl)-1-(difluoromethyl)-1H-pyrazole-3-carboxamide; and
  (7) N-(3-((2R,5S)-6-amino-3,3,5-trifluoro-2,5-dimethyl-2,3,4,5-tetrahydropyridin-2-yl)-4-fluorophenyl)-2-methyloxazole-4-carboxamide;
or a pharmaceutically acceptable salt thereof.

9. The compound of claim 1, wherein the compound is selected from the group consisting of:
  (1) N-(3-((2R,5S)-6-amino-3,3,5-trifluoro-2,5-dimethyl-2,3,4,5-tetrahydropyridin-2-yl)-4-fluorophenyl)-5-fluoropicolinamide;
  (2) N-(3-((2R,5R)-6-amino-3,3,5-trifluoro-2,5-dimethyl-2,3,4,5-tetrahydropyridin-2-yl)-4-fluorophenyl)-5-fluoropicolinamide;
  (3) N-(3-((2R,5S)-6-amino-3,3,5-trifluoro-2,5-dimethyl-2,3,4,5-tetrahydropyridin-2-yl)-4-fluorophenyl)-5-chloropicolinamide;
  (4) N-(3-((2R,5S)-6-amino-3,3,5-trifluoro-2,5-dimethyl-2,3,4,5-tetrahydropyridin-2-yl)-4-fluorophenyl)-5-cyanopicolinamide;
  (5) N-(3-((2R,5S)-6-amino-3,3,5-trifluoro-2,5-dimethyl-2,3,4,5-tetrahydropyridin-2-yl)-4-fluorophenyl)-5-methoxypyrazine-2-carboxamide;
  (6) N-(3-((2R,5S)-6-amino-3,3,5-trifluoro-2,5-dimethyl-2,3,4,5-tetrahydropyridin-2-yl)-4-fluorophenyl)-1-(difluoromethyl)-1H-pyrazole-3-carboxamide;
  (7) N-(3-((2R,5S)-6-amino-3,3,5-trifluoro-2,5-dimethyl-2,3,4,5-tetrahydropyridin-2-yl)-4-fluorophenyl)-2-methyloxazole-4-carboxamide;

(8) N-(3-((2R,5S)-6-amino-3,3,5-trifluoro-2,5-dimethyl-2,3,4,5-tetrahydropyridin-2-yl)-4-fluorophenyl)-thiazole-2-carboxamide;

(9) N-(3-((2R,5S)-6-amino-3,3,5-trifluoro-2,5-dimethyl-2,3,4,5-tetrahydropyridin-2-yl)-4-fluorophenyl)-4-bromo-1-methyl-1H-imidazole-2-carboxamide;

(10) N-(3-((2R,5S)-6-amino-3,3,5-trifluoro-2,5-dimethyl-2,3,4,5-tetrahydropyridin-2-yl)-4-fluorophenyl)-4-methylthiazole-2-carboxamide;

(11) N-(3-((2R,5S)-6-amino-3,3,5-trifluoro-2,5-dimethyl-2,3,4,5-tetrahydropyridin-2-yl)-4-fluorophenyl)-5-(trifluoromethyl)picolinamide;

(12) N-(3-((2R,5S)-6-amino-3,3,5-trifluoro-2,5-dimethyl-2,3,4,5-tetrahydropyridin-2-yl)-4-fluorophenyl)-5-methoxypyrimidine-2-carboxamide;

(13) N-(3-((2R,5S)-6-amino-3,3,5-trifluoro-2,5-dimethyl-2,3,4,5-tetrahydropyridin-2-yl)-4-fluorophenyl)-2-(difluoromethyl)oxazole-4-carboxamide;

(14) N-(3-((2R,5S)-6-amino-3,3,5-trifluoro-2,5-dimethyl-2,3,4,5-tetrahydropyridin-2-yl)-4-fluorophenyl)-4-(fluoromethyl)oxazole-2-carboxamide;

(15) N-(3-((2R,5S)-6-amino-3,3,5-trifluoro-2,5-dimethyl-2,3,4,5-tetrahydropyridin-2-yl)-4-fluorophenyl)-4-(fluoromethyl)thiazole-2-carboxamide;

(16) N-(3-((2R,5S)-6-amino-3,3,5-trifluoro-2,5-dimethyl-2,3,4,5-tetrahydropyridin-2-yl)-4-fluorophenyl)-5-(difluoromethyl)pyrazine-2-carboxamide;

(17) N-(3-((2R,5S)-6-amino-3,3,5-trifluoro-2,5-dimethyl-2,3,4,5-tetrahydropyridin-2-yl)-4-fluorophenyl)-5-methoxypicolinamide;

(18) N-(3-((2R,5S)-6-amino-3,3,5-trifluoro-2,5-dimethyl-2,3,4,5-tetrahydropyridin-2-yl)-4-fluorophenyl)-5-cyano-3-methylpicolinamide;

(19) N-(3-((2R,5S)-6-amino-3,3,5-trifluoro-2,5-dimethyl-2,3,4,5-tetrahydropyridin-2-yl)-4-fluorophenyl)-5-methoxy-3-methylpyrazine-2-carboxamide;

(20) N-(3-((2R,5S)-6-amino-3,3,5-trifluoro-2,5-dimethyl-2,3,4,5-tetrahydropyridin-2-yl)-4-fluorophenyl)-5-methyl-1,3,4-oxadiazole-2-carboxamide;

(21) N-(3-((2R,5S)-6-amino-3,3,5-trifluoro-2,5-dimethyl-2,3,4,5-tetrahydropyridin-2-yl)-4-fluorophenyl)-3-methyl-1,2,4-oxadiazole-5-carboxamide;

(22) N-(3-((2R,5S)-6-amino-3,3,5-trifluoro-2,5-dimethyl-2,3,4,5-tetrahydropyridin-2-yl)-4-fluorophenyl)-1-methyl-1H-1,2,4-triazole-3-carboxamide;

(23) N-(3-((2R,5R)-6-amino-3,3,5-trifluoro-2,5-dimethyl-2,3,4,5-tetrahydropyridin-2-yl)-4-fluorophenyl)-1-(difluoromethyl)-1H-pyrazole-3-carboxamide;

(24) N-(3-((2R,5R)-6-amino-3,3,5-trifluoro-2,5-dimethyl-2,3,4,5-tetrahydropyridin-2-yl)-4-fluorophenyl)-5-(difluoromethyl)pyrazine-2-carboxamide;

(25) N-(3-((2R,5R)-6-amino-3,3,5-trifluoro-2,5-dimethyl-2,3,4,5-tetrahydropyridin-2-yl)-4-fluoro-phenyl)-5-methoxypyrazine-2-carboxamide;

(26) N-(3-((2R,5R)-6-amino-3,3,5-trifluoro-2,5-dimethyl-2,3,4,5-tetrahydropyridin-2-yl)-4-fluorophenyl)-5-methoxypyrimidine-2-carboxamide;

(27) N-(3-((2R,5R)-6-amino-3,3,5-trifluoro-2,5-dimethyl-2,3,4,5-tetrahydropyridin-2-yl)-4-fluorophenyl)-4-methylthiazole-2-carboxamide;

(28) N-(3-((2R,5R)-6-amino-3,3,5-trifluoro-2,5-dimethyl-2,3,4,5-tetrahydropyridin-2-yl)-4-fluorophenyl)-5-(trifluoromethyl)picolinamide;

(29) N-(3-((2R,5R)-6-amino-3,3,5-trifluoro-2,5-dimethyl-2,3,4,5-tetrahydropyridin-2-yl)-4-fluorophenyl)-2-(difluoromethyl)oxazole-4-carboxamide;

(30) N-(3-((2R,5R)-6-amino-3,3,5-trifluoro-2,5-dimethyl-2,3,4,5-tetrahydropyridin-2-yl)-4-fluorophenyl)-4-(fluoromethyl)oxazole-2-carboxamide;

(31) N-(3-((2R,5R)-6-amino-3,3,5-trifluoro-2,5-dimethyl-2,3,4,5-tetrahydropyridin-2-yl)-4-fluorophenyl)-4-(fluoromethyl)thiazole-2-carboxamide;

(32) N-(3-((2R,5R)-6-amino-3,3,5-trifluoro-2,5-dimethyl-2,3,4,5-tetrahydropyridin-2-yl)-4-fluorophenyl)-5-cyanopicolinamide;

(33) N-(3-((2R,5R)-6-amino-3,3,5-trifluoro-2,5-dimethyl-2,3,4,5-tetrahydropyridin-2-yl)-4-fluoro-phenyl)-5-chloropicolinamide;

(34) N-(3-((2R,5R)-6-amino-3,3,5-trifluoro-2,5-dimethyl-2,3,4,5-tetrahydropyridin-2-yl)-4-fluorophenyl)-2-methyloxazole-4-carboxamide;

(35) N-(3-((2R,5R)-6-amino-3,3,5-trifluoro-2,5-dimethyl-2,3,4,5-tetrahydropyridin-2-yl)-4-fluorophenyl)-5-methyl-1,2,4-oxadiazole-3-carboxamide;

(36) N-(3-((2R,5R)-6-amino-3,3,5-trifluoro-2,5-dimethyl-2,3,4,5-tetrahydropyridin-2-yl)-4-fluorophenyl)-thiazole-2-carboxamide;

(37) N-(3-((2R,5R)-6-amino-3,3,5-trifluoro-2,5-dimethyl-2,3,4,5-tetrahydropyridin-2-yl)-4-fluorophenyl)-4-bromo-1-methyl-1H-imidazole-2-carboxamide;

(38) N-(3-((2R,5R)-6-amino-3,3,5-trifluoro-2,5-dimethyl-2,3,4,5-tetrahydropyridin-2-yl)-4-fluorophenyl)-1,4-dimethyl-1H-imidazole-2-carboxamide;

(39) N-(3-((2R,5R)-6-amino-3,3,5-trifluoro-2,5-dimethyl-2,3,4,5-tetrahydropyridin-2-yl)-4-fluorophenyl)-1-methyl-1H-pyrazole-3-carboxamide;

(40) N-(3-((2R,5R)-6-amino-3,3,5-trifluoro-2,5-dimethyl-2,3,4,5-tetrahydropyridin-2-yl)-4-fluorophenyl)-3-methylisoxazole-5-carboxamide;

(41) N-(3-((2R,5R)-6-amino-3,3,5-trifluoro-2,5-dimethyl-2,3,4,5-tetrahydropyridin-2-yl)-4-fluoro-phenyl)-5-methylfuran-2-carboxamide;

(42) N-(3-((2R,5R)-6-amino-3,3,5-trifluoro-2,5-dimethyl-2,3,4,5-tetrahydropyridin-2-yl)-4-fluorophenyl)-2-methyloxazole-5-carboxamide;

(43) N-(3-((2R,5R)-6-amino-3,3,5-trifluoro-2,5-dimethyl-2,3,4,5-tetrahydropyridin-2-yl)-4-fluorophenyl)-5-(methoxy-$d_3$)picolinamide;

(44) N-(3-((2R,5R)-6-amino-3,3,5-trifluoro-2,5-dimethyl-2,3,4,5-tetrahydropyridin-2-yl)-4-fluorophenyl)-4-chlorobenzamide;

(45) N-(3-((2R,5S)-6-amino-3,3,5-trifluoro-2,5-dimethyl-2,3,4,5-tetrahydropyridin-2-yl)-4-fluorophenyl)-5-(difluoromethoxy)picolinamide;

(46) N-(3-((2R,5S)-6-amino-3,3,5-trifluoro-2,5-dimethyl-2,3,4,5-tetrahydropyridin-2-yl)-4-fluorophenyl)-3-fluoro-5-methoxypicolinamide;

(47) N-(3-((2R,5S)-6-amino-3,3,5-trifluoro-2,5-dimethyl-2,3,4,5-tetrahydropyridin-2-yl)-4-fluorophenyl)-2,5-dimethyloxazole-4-carboxamide;

(48) N-(3-((2R,5S)-6-amino-3,3,5-trifluoro-2,5-dimethyl-2,3,4,5-tetrahydropyridin-2-yl)-4-fluorophenyl)-5-(methoxy-$d_3$)picolinamide; and

(49) N-(3-((2R,5S)-6-amino-3,3,5-trifluoro-2,5-dimethyl-2,3,4,5-tetrahydropyridin-2-yl)-4-fluorophenyl)-5-fluoro-3-methylpicolinamide;

or a pharmaceutically acceptable salt thereof.

10. The compound of claim 8, wherein the compound is selected from the group consisting of:

(1) N-(3-((2R,5S)-6-amino-3,3,5-trifluoro-2,5-dimethyl-2,3,4,5-tetrahydropyridin-2-yl)-4-fluorophenyl)-5-fluoropicolinamide, and (2) N-(3-((2R,5S)-6-amino-3,3,5-trifluoro-2,5-dimethyl-2,3,4,5-tetrahydropyridin-2-yl)-4-fluorophenyl)-5-methoxypyrazine-2-carboxamide;
or a pharmaceutically acceptable salt thereof.

11. A pharmaceutical composition comprising the compound of claim 1 or a pharmaceutically acceptable salt thereof and a pharmaceutically acceptable carrier.

12. A method of treating Alzheimer's disease comprising administering a therapeutically effective amount of the compound of claim 1 to a patient in need thereof.

13. The compound of claim 9, wherein the compound is selected from the group consisting of:
  (1) N-(3-((2R,5S)-6-amino-3,3,5-trifluoro-2,5-dimethyl-2,3,4,5-tetrahydropyridin-2-yl)-4-fluorophenyl)-5-methoxypicolinamide,
  (2) N-(3-((2R,5R)-6-amino-3,3,5-trifluoro-2,5-dimethyl-2,3,4,5-tetrahydropyridin-2-yl)-4-fluorophenyl)-5-cyano-3-methylpicolinamide, and
  (3) N-(3-((2R,5R)-6-amino-3,3,5-trifluoro-2,5-dimethyl-2,3,4,5-tetrahydropyridin-2-yl)-4-fluorophenyl)-5-(difluoromethyl)pyrazine-2-carboxamide;
or a pharmaceutically acceptable salt thereof.

14. A compound according to claim 1 wherein the compound is N-(3-((2R,5S)-6-amino-3,3,5-trifluoro-2,5-dimethyl-2,3,4,5-tetrahydropyridin-2-yl)-4-fluoro-phenyl)-5-chloropicolinamide.

15. A compound according to claim 1 wherein the compound is N-(3-((2R,5S)-6-amino-3,3,5-trifluoro-2,5-dimethyl-2,3,4,5-tetrahydropyridin-2-yl)-4-fluoro-phenyl)-5-cyanopicolinamide.

16. A compound according to claim 1, wherein the compound is N-(3-((2R,5S)-6-amino-3,3,5-trifluoro-2,5-dimethyl-2,3,4,5-tetrahydropyridin-2-yl)-4-fluoro-phenyl)-5-methoxypyrazine-2-carboxamide.

17. A compound according to claim 1, wherein the compound is N-(3-((2R,5S)-6-amino-3,3,5-trifluoro-2,5-dimethyl-2,3,4,5-tetrahydropyridin-2-yl)-4-fluoro-phenyl)-1-(difluoromethyl)-1H-pyrazole-3-carboxamide.

18. A compound according to claim 1, wherein the compound is N-(3-((2R,5S)-6-amino-3,3,5-trifluoro-2,5-dimethyl-2,3,4,5-tetrahydropyridin-2-yl)-4-fluoro-phenyl)-5-methoxypicolinamide.

19. A compound according to claim 1, wherein the compound is N-(3-((2R,5S)-6-amino-3,3,5-trifluoro-2,5-dimethyl-2,3,4,5-tetrahydropyridin-2-yl)-4-fluoro-phenyl)-5-cyano-3-methylpicolinamide.

20. A compound according to claim 1, wherein the compound is N-(3-((2R,5R)-6-amino-3,3,5-trifluoro-2,5-dimethyl-2,3,4,5-tetrahydropyridin-2-yl)-4-fluoro-phenyl)-5-(difluoromethyl)pyrazine-2-carboxamide.

21. A compound according to claim 1, wherein the compound is N-(3-((2R,5S)-6-amino-3,3,5-trifluoro-2,5-dimethyl-2,3,4,5-tetrahydropyridin-2-yl)-4-fluoro-phenyl)-2,5-dimethyloxazole-4-carboxamide.

22. A compound according to claim 1, wherein the compound is N-(3-((2R,5S)-6-amino-3,3,5-trifluoro-2,5-dimethyl-2,3,4,5-tetrahydropyridin-2-yl)-4-fluorophenyl)-5-(methoxy-$d_3$)picolinamide.

* * * * *

UNITED STATES PATENT AND TRADEMARK OFFICE
CERTIFICATE OF CORRECTION

PATENT NO. : 9,353,084 B2
APPLICATION NO. : 14/625658
DATED : May 31, 2016
INVENTOR(S) : Karsten Juhl et al.

Page 1 of 1

It is certified that error appears in the above-identified patent and that said Letters Patent is hereby corrected as shown below:

In the claims (1) Claim 13, Column 61, Line 16, "(2R,5R)" should read -- (2R,5S) --.

Signed and Sealed this
Second Day of August, 2016

Michelle K. Lee
*Director of the United States Patent and Trademark Office*